US008318210B2

(12) United States Patent
Tengler et al.

(10) Patent No.: US 8,318,210 B2
(45) Date of Patent: Nov. 27, 2012

(54) COMPOSITIONS AND METHODS OF MAKING SUSTAINED RELEASE LIQUID FORMULATIONS

(75) Inventors: Mark Tengler, Colleyville, TX (US); Paul Taskey, Richland Hills, TX (US); Daniel Lockhart, Euless, TX (US); Russ McMahen, Flower Mound, TX (US)

(73) Assignee: Neos Therapeutics, LP, Grand Prairie, TX (US)

( * ) Notice: Subject to any disclaimer, the term of this patent is extended or adjusted under 35 U.S.C. 154(b) by 1342 days.

(21) Appl. No.: 11/068,124

(22) Filed: Feb. 28, 2005

(65) Prior Publication Data

US 2006/0193877 A1 Aug. 31, 2006

(51) Int. Cl.
*A61K 9/14* (2006.01)

(52) U.S. Cl. .......................... 424/501; 424/400; 424/490

(58) Field of Classification Search .................. None
See application file for complete search history.

(56) References Cited

U.S. PATENT DOCUMENTS

| | | | |
|---|---|---|---|
| 3,173,876 A | 3/1965 | Zobrist | |
| 3,276,586 A | 10/1966 | Rosaen | |
| 3,541,005 A | 11/1970 | Strathmann et al. | |
| 3,541,006 A | 11/1970 | Bixler et al. | |
| 3,546,142 A | 12/1970 | Michaels et al. | |
| 4,285,987 A | 8/1981 | Ayer et al. | |
| 4,438,150 A * | 3/1984 | Gantwerker et al. | 426/625 |
| 4,692,462 A * | 9/1987 | Banerjee | 424/444 |
| 5,368,852 A * | 11/1994 | Umemoto et al. | 424/78.1 |
| 5,563,177 A * | 10/1996 | Popli et al. | 514/718 |
| 5,672,358 A * | 9/1997 | Tabibi et al. | 424/450 |
| 5,674,533 A | 10/1997 | Santus et al. | |
| 5,980,882 A * | 11/1999 | Eichman | 424/78.12 |
| 5,980,945 A | 11/1999 | Ruiz | |
| 6,039,470 A * | 3/2000 | Conwell | 366/137 |
| 6,120,787 A | 9/2000 | Gustafsson et al. | |
| 6,550,955 B2 | 4/2003 | D'Silva | |
| 6,613,358 B2 | 9/2003 | Randolph et al. | |
| 6,709,675 B1 | 3/2004 | Lombardin et al. | |
| 6,818,018 B1 | 11/2004 | Sawhney | |
| 6,838,449 B2 | 1/2005 | Asgharian | |
| 2003/0077297 A1* | 4/2003 | Chen et al. | 424/400 |
| 2003/0108575 A1* | 6/2003 | Lu | 424/400 |
| 2003/0175408 A1* | 9/2003 | Timm et al. | 427/2.1 |

OTHER PUBLICATIONS

Remington: The Science and Practice of Pharmacy, 20th edition, p. 341-343, 2000.*
"About Triblender mixer Equipment", http://www.fraingroup.com/sub_cat_Mixer-Liquid_153_Triblender_253.html, accessed Dec. 11, 2008.*

(Continued)

*Primary Examiner* — Nissa Westerberg
(74) *Attorney, Agent, or Firm* — Hunton & Williams

(57) ABSTRACT

The present invention includes compositions and methods for the controlled release of active agents in a shelf-stable liquid formulation by blending one or more controlled release microbeads comprising one or more active agents, preparing a dense, thixotropic solution having a density that is at, or about, the density of the one or more microbeads comprising a thixotropic agent, water and one or more preservatives under conditions that reduce bubble formation and mixing the microbeads and the thixotropic solutions in a mixer that lacks scraping paddles.

34 Claims, 8 Drawing Sheets

OTHER PUBLICATIONS

SXJ Series Side-Entering Mixers, http://www.lightninmixers.com/sxj_series.asp, accessed Dec. 11, 2008.*

Axial Flow Impellers, http://www.lightninmixers.com/axial_flow_imps.asp, accessed Dec. 11, 2008.*

Amberlite® IRP64 product information page from Rohm-Haas, accessed Dec. 11, 2008.*

"Understanding Hihg-Viscosity Mxiing", Adhesive Magazine, Jun. 1, 2000.*

PCT Search Report and Written Opinion of the International Searching Authority for PCT/US2006/006670, dated Nov. 22, 2006.

Dolz, M. et al., "A time-dependent expression for thixotropic areas. Application to Aerosil 200 hydrogels," J. Pharm. Sci. (2000), vol. 89, No. 6, pp. 790-797.

Franck, "New Approach to Characterize Starch Dispersions", TA Instruments, Retrieved from the Internet at www.tainstruments.com.tw/library_download.aspx?...New_approach-to_characterize_starch_dispersions . . . , Date Unknown.

Tang et al., "Drum Drying", Encyclopedia of Agricultural Food and Biological Engineering, pp. 211-214, (2003).

First Office Action of the State Intellectural Property Office of the People's Republic of China issued Oct. 23, 2009 in Patent Application No. 200680014802.1.

* cited by examiner

COMPOSITIONS AND METHODS OF MAKING SUSTAINED RELEASE LIQUID FORMULATIONS

FIELD OF INVENTION

The invention relates to compositions and methods of making liquid, sustained-release formulations, and more particularly, to the use of methods that eliminate the problems associated with the manufacture of the same.

BACKGROUND OF THE INVENTION

Without limiting the scope of the invention, its background is described in connection with pharmaceutical agents that are delivered in an extended or sustained-release form, as an example.

One such method of making sustained release particles is taught in U.S. Pat. No. 6,120,787, issued to Gustafsson, et al, which teach a method of preparing parenterally administrable sustained release microparticles, that include preparing core particles in an aqueous medium that is essentially free from organic solvent, a biologically active substance being entrapped therein during or after said preparation, drying the core particles and coating the same with a release-controlling polymer by air suspension technique so as to create a shell on the core particles without any detrimental exposure of the active substance to organic solvent.

Another sustained-release composition includes an amorphous polymer are taught in U.S. Pat. No. 6,613,358, issued to Randolph, et al., which provided for a sustained release composition for sustained release of a pharmaceutical substance that includes a biocompatible polymer that is highly amorphous and a pharmaceutical substance in a hydrophobic ion complex with an amphiphilic material. A compressed antisolvent method for manufacturing the composition it taught as are various product forms incorporating the composition and various uses for the composition.

Yet another sustained release drug formulation is taught in U.S. Pat. No. 5,980,945, issued to Ruiz in which a sustained release drug formulation includes a drug; a biodegradable polymer that is insoluble in water; and an oil vehicle in which both the drug and the polymer are dissolved. The oil vehicle contains 10-100% by volume of a pharmaceutically acceptable oil and 0-90% by volume a pharmaceutically acceptable liquid carrier for the drug or the polymer.

Finally, U.S. Pat. No. 5,674,533 issued to Santus, et al., teaches pharmaceutical compositions for the controlled release of the anti-tussive, moguisteine, in a liquid suspension designed either as ready-to-use and time-stable liquid formulations with a shelf-life of at least two years, or as dry formulations that are reconstituted with water when needed and then remain stable throughout the treatment period. Santus teaches the use of coated microgranules for the controlled release of moguisteine having sizes ranging from 50 to 500 μm, preferably from 90 to 300 μm, which are capable of remaining easily in suspension in a liquid for extended times. The microgranules have moguisteine core, with one or more optional plasticizers and excipients, granulated into microgranules having sizes smaller than 500 μm, uniform surfaces, substantially spherical shapes, apparent densities of about 500 to 600 g/l and very low friabilities, made by wet-kneading micronised moguisteine using water or a mixture of water and other solvents. These initial microgranules are given controlled-release properties by, a first coating having essentially hydrophilic characteristics, which isolates the microgranules; a second coating having lipophilic characteristics on top of the first coating; and a third coating having hydrophilic characteristics.

SUMMARY OF THE INVENTION

The present invention addressed the problems associated with the delivery of one or more active agents in a liquid dosage form under controlled conditions. Liquid formulations are preferred by many users due to the easy of delivery, namely, swallowing thereby leading to increased compliance with dosing regimens. It has been found that many children and adults fail to comply with dosing instructions due to the size, shape, taste and/or mouth-feel of, e.g., tablets, caplets and even gelcaps.

The present inventors have recognized that delivery of agents in liquid formulation is not only preferred by many users, but also that many of the materials and processing methods and equipment using in the industry today fail to deliver products and formulations that, e.g., are shelf-stable, do not separate on the shelf (both floating and settling), do not require vigorous shaking (which greatly affects dosing consistency), the mouth-feel of the liquid (e.g., grainy, bitter, slimy), provide actual controlled, sustained, mixed or modified release. Finally, it was recognized that despite many decades of research and development, controlled-release formulations have not been amenable to large-scale production in facilities and to amounts that are permissible for industrial applicability of controlled-release liquid formulations.

Furthermore, it was found that many known techniques for eliminating the problems commonly associated with the manufacture of controlled-release liquid formulations, and hence their widespread failure, did not solve the problems. Examples of techniques that failed in certain forms of the development of the present invention included: inert gas sparging, vacuum, reducing mixer speeds and eliminating mixer (e.g., propeller) caviation in the mixing vessel. Despite using these techniques individually and in combination, none of these techniques solved the problems of, e.g., separation and stability. A novel approach was needed to reach the present invention.

Following a detailed analysis of the many failures, it was found that several problems associated with the actual manufacturing steps and the compositions used were needed to address the problems solved herein. For example, it was observed that one problem associated with the use of controlled release beads, many examples of which are well-known in the art, was the dissociation of the bead coating during mixing, in which mixer paddles designed to scrape the sides of the vessels to increase mixing efficiency were also causing the beads to shear and break, thereby eliminating the sustained-release nature of the beads. Another example was the floating of beads as the liquid formulation was tested for shelf-stability, as air bubbles introduced during the manufacturing process were found to cling to, or form on, the beads thereby changing their nominal density from that calculated based on its manufacture.

More particularly, the present invention includes compositions and methods for preparing a liquid, controlled-release formulation by blending one or more controlled release microbeads having one or more active agents, preparing a dense, thixotropic solution having a density that is at or about the density of the one or more microbeads, wherein a thixotropic agent, water and one or more preservatives are mixed under conditions that reduce bubble formation, e.g., using a mixer that lacks scraping paddles. The one or more microbeads may include an enteric coat, a resin coat, a lacquer coat, a pH-sensitive coating, a biodegradable polymer matrix, a water soluble matrix, an ionic matrix, combinations and mixtures thereof. The one or more microbeads may also includes one or more polymers selected from cellulose, ethylcellulose, methylcellulose, propylcellulose, methoxypropylcellulose, cellulose nitrate, poly(vinyl alcohol), poly(vinyl chloride), polystyrene, polyethylene, polypropylene, poly(ethylene-co-vinyl acetate), poly(hydroxybutyric acid), poly(hydroxyvalerianic acid-co-hydroxybutyric acid), poly(lactic acid), poly(glycolic acid), poly(lactic acid-co-glycolic acid), poly($\epsilon$-caprolactones), poly($\epsilon$-caprolactone-co-DL-lactic acid), poly(maleic anhydride), polyamides, gelatin, chitosan, collagen, poly(hydroxyalkyl)-L-glutamines, poly($\gamma$-ethyl-L-glutaminate-co-glutamic acid), poly(L-leucine-co-L-aspartic acid), poly(proline-co-glutamic acid), poly(alkyl 2-cyanoacrylates), polyurethanes, poly(methyl methacrylate), poly(methyl methacrylate-co-methacrylic acid) and poly(methacrylate-co-hydroxypropyl methacrylate), polystyrene, polistirex, polacrilex and salts, combinations and mixtures thereof.

The method of the present invention increases the shelf-life and stability of the actives agents, e.g., by preventing the separation of the components by taking steps to reduce or eliminate bubble formation during the manufacture of the controlled-release liquid formulation of the present invention. Steps of the present invention for minimizing, reducing and/or eliminating bubble formation include, but are not limited to using the following steps alone or in combination: using a diaphragm pump to combine, e.g., the water and the thixotropic agent and one or more preservatives, colorants and flavorants; placing the recirculating tube below the surface of the liquid; adding liquids along the side of a vessel holding the liquid; sprinkling beads (e.g., one or more beads that includes one or more active agents) onto the surface of the liquid; mixing the solution in the absence of one or more paddles that scrape the vessel; mixing the solution with a propeller mixer; mixing the solution with a propeller mixer at a speed that reduces or minimizes cavitation and combinations of two or more of these steps.

The controlled-release liquid formulation may include a portion of the one or more beads with an immediate release profile and another portion with a controlled or delayed release profile. When using an ion-exchange matrix, bead or resin to retain the one or more active agents the liquid solution will in some cases be a low-ionic strength, depending on the nature of the ion-exchange matrix and the one or more active agents. The skilled artisan can easily determine the best matrix for a particular active, determine the amount of loading (theoretical and empirical), and the conditions for retention and release.

Examples of active agents that may be provided as part of the liquid formulations of the present invention include vitamins, minerals, nutritional supplements, herbal extracts, gums, gels, oils, salts, mixtures and combinations thereof. Pharmaceutical active agents may include, e.g., protein, peptide, carbohydrate, polysaccharide, glycoprotein, lipid, hormone, growth factor, cytokine, interferon, receptor, antigen, allergen, antibody, antiviral, antifungal, antihelminthic, substrate, metabolite, cofactor, inhibitor, drug, nutrient, toxin, poison, explosive, pesticide, chemical warfare agent, biowarfare agent, biohazardous agent, infectious agent, prion, radioisotope, vitamin, heterocyclic aromatic compound, carcinogen, mutagen, narcotic, amphetamine, barbiturate, hallucinogen. In some cases the liquid may be, eg., a vaccine for against a virus, bacterium, helminth and/or fungi, fragments, receptors or toxins thereof, e.g., *Salmonella, Streptococcus, Brucella, Legionella, E. coli, Giardia, Cryptosporidium, Rickettsia*, spore, mold, yeast, algae, amoebae, dinoflagellate, unicellular organism, pathogen, cell, combinations and mixtures thereof. The one or more active agents may be a pharmaceutical agent, an enzyme, a cytokine, a growth promoting agent, an antibody, an antigen, a hormone, a vaccine, a cell, a live-attenuated pathogen, a heat-killed pathogen, a virus, a bacteria, a fungi, a peptide, a carbohydrate, a nucleic acid, a lipid, mixtures and combinations thereof.

Specific examples of active agents include: steroids, respiratory agents, sympathomimetics, local anesthetics, antimicrobial agents, antiviral agents, antifungal agents, antihelminthic agents, insecticides, antihypertensive agents, antihypertensive diuretics, cardiotonics, coronary vasodilators, vasoconstrictors, β-blockers, antiarrhythmic agents, calcium antagonists, anti-convulsants, agents for dizziness, tranquilizers, antipsychotics, muscle relaxants, drugs for Parkinson's disease, respiratory agents, hormones, non-steroidal hormones, antihormones, vitamins, antitumor agents, miotics, herb medicines, herb extracts, antimuscarinics, interferons, immunokines, cytokines, muscarinic cholinergic blocking agents, mydriatics, psychic energizers, humoral agents, antispasmodics, antidepressant drugs, anti-diabetics, anorectic drugs, anti-allergenics, decongestants, expectorants, antipyretics, antimigrane, anti-malarials, anti-ulcerative, anti-estrogen, anti-hormone agents, anesthetic agent, or drugs having an action on the central nervous system. For example, for use in the treatment of cold/cough symptoms the active agents may include one or more antihistamines, antitussives, expectorants and the like, e.g., pseudoephedrine, chlorpheniramine, dextromethorphan, guaifenesin, and salts thereof or mixtures of salts thereof. The liquid formulation may also include an analgesic or even a narcotic.

Examples of carriers for the actives of the present invention include any degradable, partially degradable or non-degradable and generally biocompatible polymer, e.g., polystirex, polypropylene, polyethylene, polacrilex, poly-lactic acid (PLA), polyglycolic acid (PGA) and/or poly-lactic polyglycolic acid (PGLA) in the form or a matrix or even a bead.

The present invention also includes those liquid formulations made by the methods disclosed and claimed herein. For example, specific liquid formulation may include one or more active agents available for immediate, modified and/or extended or controlled release for use in treating cold/cough/allergy symptoms. The one or more actives for cold/cough/allergy may include one or more of the following: anti-tussives, anti-histamines, expectorants and analgesics. For example, the actives may include: pseudoephedrine, chlorpheniramine, dextromethorphan, guaifenesin, and salts thereof or mixtures of salts thereof.

In another embodiment, the present invention includes a method for preparing a liquid, controlled-release formulation by blending one or more controlled release beads having one or more active agents with a dense, thixotropic solution having a density that is at or about the density of the one or more beads and a thixotropic agent, water and one or more preservatives under conditions that reduce bubble formation. A liquid formulation is made by the method. Yet another method for preparing a liquid, controlled-release formulation includes blending a mixture comprising one or more controlled-release beads comprising one or more active agents, a thickening agent and a surfactant by mixing with a low cavitation propeller and recirculating the mixture under the surface of the mixture so as to minimize bubble formation. In one embodiment, the formulation includes between about 15-45 mg phenylephrine disposed in, on or about a resin, between about 2-8 mg chlorphineramine disposed in, on or about a resin per dose. The formulation may also include between about 15-45 mg dextromethorphan disposed in, on or about a resin.

Yet another embodiment of the present invention is a method of preparing a liquid, controlled-release formulation by blending a mixture comprising one or more active agents on or about a carrier a thickening agent under conditions that minimize the introduction of air. The conditions that minimize, reduce and/or eliminate the introduction of air and/or air bubbles include one or more of the following steps used alone, in combination and/or in any order: using a diaphragm pump to combine, e.g., the water and the thixotropic agent and one or more preservatives, colorants and flavorants; placing the recirculating tube below the surface of the liquid; adding liquids along the side of a vessel holding the liquid; sprinkling beads (e.g., one or more beads that includes one or more active agents) onto the surface of the liquid; mixing the solution in the absence of one or more paddles that scrape the vessel; mixing the solution with a propeller mixer; mixing the solution with a propeller mixer at a speed that reduces or minimizes cavitation and combinations of two or more of these steps.

Yet another method for preparing a liquid, controlled-release formulation of the present invention includes blending a mixture of one or more controlled-release beads with one or more active agents on a carrier in a solution having a low ionic concentration and a thixotropic agent, under conditions that minimize the introduction of air bubbles.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
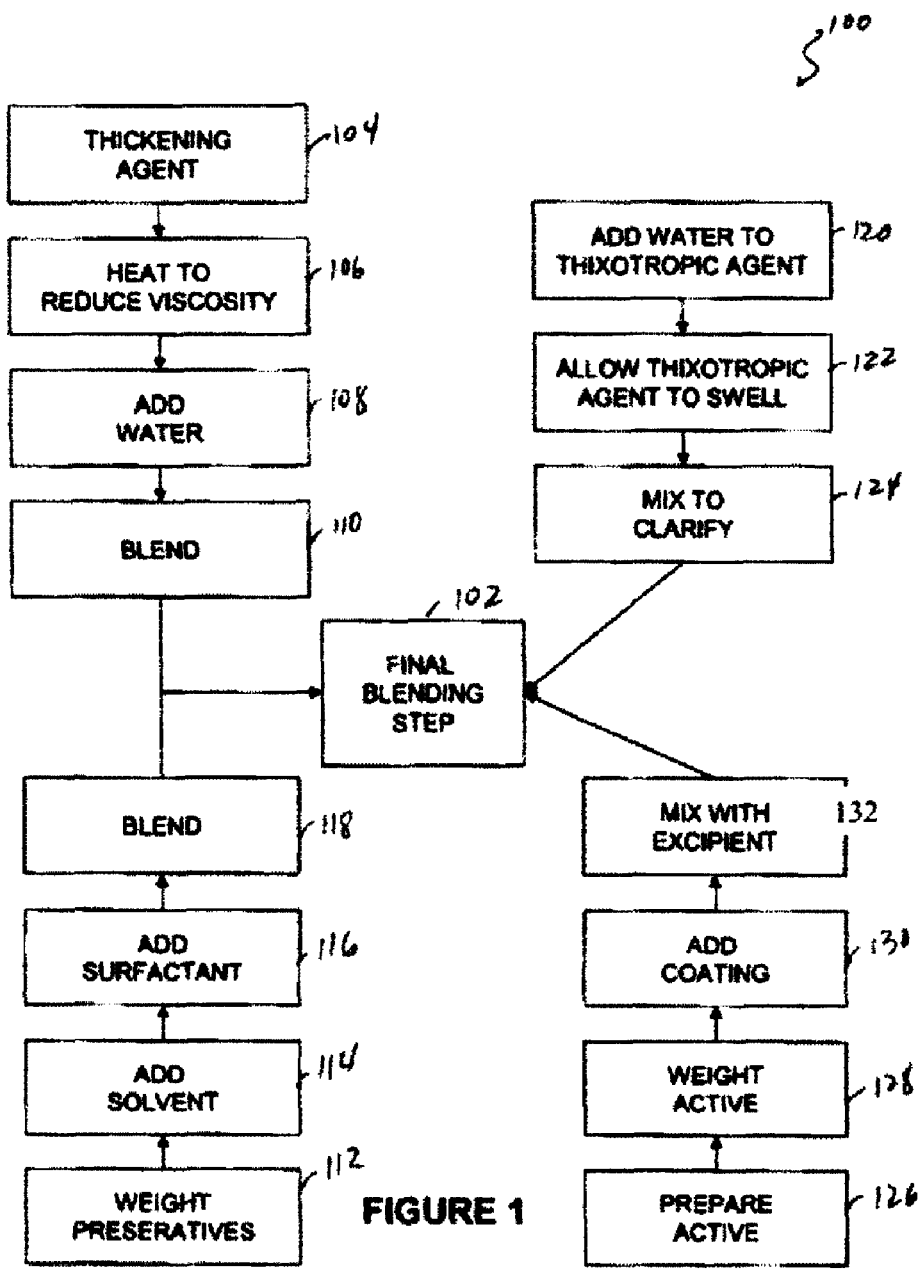
FIG. 1 is a flow-chart of the basic steps of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the terms "extended release," "sustained release," and "delayed release" are used to define a release profile to effect delivery of an active over an extended period of time, defined herein as being between about 60 minutes and about 2, 4, 6, 8 or even 12 hours. Extended release may also be defined functionally as the release of over 80 to 90 percent (%) of the active ingredient after about 60 minutes and about 2, 4, 6 or even 8 hours. Extended release as used herein may also be defined as making the active ingredient available to the patient or subject regardless of uptake, as some actives may never be absorbed by the animal. Various extended release dosage forms may be designed readily by one of skill in art as disclosed herein to achieve delivery to both the small and large intestines, to only the small intestine, or to only the large intestine, depending upon the choice of coating materials and/or coating thickness.

"Extended release" and "delayed release" formulations may be prepared and delivered so that release is accomplished at some generally predictable location in the lower intestinal tract more distal to that which would have been accomplished if there had been no delayed release alterations. A method for delay of release is, e.g., a coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present invention to achieve delivery to the lower gastrointestinal tract. Polymers and compatible mixtures thereof may be used to provide the coating for the delayed or the extended release of active ingredients, and some of their properties, include, but are not limited to: shellac, also called purified lac, a refined product obtained from the resinous secretion of an insect. This coating dissolves in media of pH>7.

As used herein, the term "thixotropic" is used to describe one or more agents, e.g., certain gels, which liquefy when subjected to vibratory forces like simple shaking, and then solidify again when left standing. Thixotropic behavior is observed when long-chain molecules tend to orient themselves in the direction of flow; as the applied force is increased, the resistance to flow is decreased. Yet when high shear stress is removed, the solution will quickly revert to its original viscous state. Some celluloses exhibit thixotropic behavior wherein the solution returns to its viscous state over a period of time. Examples of thixotropic agents for use with, e.g., food, pharmaceuticals, are well known in the art, e.g., "A time-dependent expression for thixotropic areas. Application to Aerosil 200 hydrogels," M. Dolz, F. González, J. Delegido, M. J. Hernandez, J. Pellicer, J. Pharm. Sci., Vol. 89, No. 6, pages 790-797 (2000), relevant portions incorporated herein by reference. Numerous examples of thixotropic agents, such as cellulose (e.g., carboxymethylcellulose), gums (e.g., xanthan), collagen, gelatin, aerogels and others are well known in the art and may be used with the present invention, e.g., U.S. Pat. Nos. 6,709,675; 6,838,449; 6,818,018, relevant portions incorporated herein by reference.

The pharmaceutical composition and/or the solid carrier particles can be coated with one or more enteric coatings, seal coatings, film coatings, barrier coatings, compress coatings, fast disintegrating coatings, or enzyme degradable coatings. Multiple coatings may be applied for desired performance. Further, one or more of the actives may be provided for immediate release, pulsatile release, controlled release, extended release, delayed release, targeted release, synchronized release, or targeted delayed release. In fact, the formulation may include combinations of typical pharmaceutical actives (e.g., pseudephedrin) and vitamins (e.g., Vitamin C), minerals (Ca, Mg, Zn, K) or other supplements (e.g., St. John's Wort, echinacae, amino acids). For release/absorption control, solid carriers can be made of various component types and levels or thicknesses of coats, with or without an active ingredient. Such diverse solid carriers can be blended in a dosage form to achieve a desired performance. The liquid formulations may be delivered to, and adapted for, oral, nasal, buccal, ocular, urethral, transmucosal, vaginal, topical or rectal delivery, although oral delivery is used mostly.

When formulated with microparticles or nanoparticles, the one or more actives the release profile can easily be adapted by adding, e.g., a hard or soft gelatin coating, a starch coating, a resin or polymer coating and/or a cellulosic coating. Although not limited to microparticles or nanoparticles (as in, e.g., microcapsules or nanocapsules), such dosage forms may be further coated with, for example, a seal coating, an enteric coating, an extended release coating, or a targeted delayed release coating. The term "enteric coating" as used herein relates to a mixture of pharmaceutically acceptable excipients that is applied to, combined with, mixed with or otherwise added to the carrier or composition. The coating may be applied to an active that is compressed, molded or extruded and may also include: gelatin, and/or pellets, beads, granules or particles of the carrier or composition. The coating may be applied through an aqueous dispersion or after dissolving in appropriate solvent. The carrier may or may not be fully or partially biodegradable.

Carriers for use with the present invention include permeable and semipermeable matrices or polymers that control the release characteristics of the formulation. Such polymers include, for example, cellulose acylates, acetates, and other semi-permeable polymers such as those described in U.S. Pat. No. 4,285,987 (hereby incorporated by reference), as well as the selectively permeable polymers formed by the coprecipitation of a polycation and a polyanioni as disclosed in U.S. Pat. Nos. 3,173,876; 3,276,586; 3,541,005; 3,541,006 and 3,546,142 (relevant portions incorporated herein by reference).

Other carriers for use with the present invention include, e.g., starch, modified starch, and starch derivatives, gums, including but not limited to xanthan gum, alginic acid, other alginates, benitoniite, veegum, agar, guar, locust bean gum, gum arabic, quince psyllium, flax seed, okra gum, arabinoglactin, pectin, tragacanth, scleroglucan, dextran, amylose, amylopectin, dextrin, etc., cross-linked polyvinylpyrrolidone, ion-exchange resins, such as potassium polymethacrylate, carrageenan (and derivatives), gum karaya, biosynthetic gum, etc. Other useful polymers include: polycarbonates (linear polyesters of carbonic acid); microporous materials (bisphenol, a microporous poly(vinylchloride), micro-porous polyamides, microporous modacrylic copolymers, microporous styrene-acrylic and its copolymers); porous polysulfones, halogenated poly(vinylidene), polychloroethers, acetal polymers, polyesters prepared by esterification of a dicarboxylic acid or anhydride with an alkylene polyol, poly(alkylenesulfides), phenolics, polyesters, asymmetric porous polymers, cross-linked olefin polymers, hydrophilic microporous homopolymers, copolymers or interpolymers having a reduced bulk density, and other similar materials, poly(urethane), cross-linked chain-extended poly(urethane), poly(imides), poly(benzimidazoles), collodion, regenerated proteins, semi-solid cross-linked poly(vinylpyrrolidone).

Additional additives and their levels, and selection of a primary coating material or materials will depend on the following properties: resistance to dissolution and disintegration in the stomach; impermeability to gastric fluids and drug/carrier/enzyme while in the stomach; ability to dissolve or disintegrate rapidly at the target intestine site; physical and chemical stability during storage; non-toxicity; easy application as a coating (substrate friendly); and economical practicality.

Dosage forms of the compositions of the present invention can also be formulated as enteric coated delayed release oral dosage forms, i.e., as an oral dosage form of a pharmaceutical composition as described herein that uses an enteric coating to effect release in the lower gastrointestinal tract. The enteric coated dosage form will generally include microparticles, microgranules, micropellets or microbeads of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

Active Pharmaceutical Ingredients. The one or more active agents that are formulated in a self-stable manner using the present invention may include a wide variety of uses, not just the traditional pharmaceutical agents. Actives for use with the present invention in immediate and/or controlled release formulations may include systemically active therapeutic agents, locally active therapeutic agents, disinfecting agents, chemical impregnants, cleansing agents, deodorants, fragrances, dyes, animal repellents, insect repellents, fertilizing agents, pesticides, herbicides, fungicides, and plant growth stimulants, and the like. Some non-limiting examples of active agents are listed hereinbelow. Those skilled in the art will appreciate that any of these compounds may be used in the form of their pharmaceutically acceptable salt forms, e.g., carboxylic acids, with counter-ions, e.g., potassium, sodium, calcium; as ionic combinations with, e.g., resins, polymers, beads, matrices; with sugars or sugar derivatives, e.g., malate, tannate; amino acids, lipids, oils or combinations, mixtures and the like. In some embodiments, the present inventors have found that certain actives may be provided with two different salts, each of which may have a different solubility and/or release profile under, e.g., physiologic conditions. In fact, liquid formulation of present invention includes combinations of one or more of the following: immediate release, pulsatile release, controlled release, extended release, delayed release, targeted release, or targeted delayed release.

Some examples of active ingredients suitable for use in the pharmaceutical formulations and methods of the present invention include: hydrophilic, lipophilic, amphiphilic or hydrophobic, and that can be solubilized, dispersed, or partially solubilized and dispersed, on or about a carrier. The active agent-carrier combination may be coated further to encapsulate the agent-carrier combination. Alternatively, an active ingredient may also be provided separately from the solid pharmaceutical composition, such as for co-administration. Such active ingredients can be any compound or mixture of compounds having therapeutic or other value when administered to an animal, particularly to a mammal, such as drugs, nutrients, cosmaceuticals, nutraceuticals, diagnostic agents, nutritional agents, and the like. The active agents listed below may be found in their native state, however, they will generally be provided in the form of a salt. The active agents listed below include their isomers, analogs and derivatives.

In one embodiment, the active ingredient agent is hydrophobic. Hydrophobic active ingredients are compounds with little or no water solubility. Intrinsic water solubilities (i.e., water solubility of the unionized form) for hydrophobic active ingredients are less than about 1% by weight, and typically less than about 0.1% or 0.01% by weight. Suitable hydrophobic active ingredients are not limited by therapeutic category, and can be, for example, analgesics, anti-inflammatory agents, antihelmimthics, anti-arrhythmic agents, antibacterial agents, anti-viral agents, anti-coagulants, anti-depressants, anti-diabetics, anti-epileptics, anti-fungal agents, anti-gout agents, anti-hypertensive agents, anti-malariale, anti-migrainc agents, anti-muscarinic agents, anti-neoplastic agents, crectile dysfunction improvement agents, immunosuppressants, anti-protozoal agents, anti-thyroid agents, anxiolytic agents, sedatives, hypnotics, neuroleptics, .beta.-Blockers, cardiac inotropic agents, corticosteroids, diuretics, anti-parkinsonian agents, gastro-intestinal agents, histamine receptor antagonists, keratolytics, lipid regulating agents, anti-anginal agents, cox-2 inhibitors, leukotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, and mixtures thereof. Salts, isomers and derivatives of the above-listed hydrophobic active ingredients may also be used, as well as combinations and mixtures thereof.

Other examples of suitable hydrophobic active ingredients include: acetretin, albendazole, albuterol, aminoglutethimide, amiodarone, amlodipine, amphetamine, amphotericin B, atorvastatin, atovaquone, azithromycin, baclofen, beclomethasone, benezepril, benzonatate, betamethasone, bicalutamide, budesonide, bupropion, busulfan, butenafine, calcifediol, calcipotriene, calcitriol, camptothecin, candesartan, capsaicin, carbamezepine, carotenes, celecoxib, cerivastatin, cetirizine, chlorpheniramine, cholecalciferol, cilostazol, cimetidine, cinnarizine, ciprofloxacin, cisapride, clarithromycin, clemastine, clomiphene, clomipramine, clopidogrel, codeine, coenzyme Q10, cyclobenzaprine, cyclosporin, danazol, dantrolene, dexchlorpheniramine, diclofenac, dicoumarol, digoxin, dehydroepiandrosterone, dihydroergotamine, dihydrotachysterol, dirithromycin, donezepil, efavirenz, eposartan, ergocalciferol, ergotamine, essential fatty acid sources, etodolac, etoposide, famotidine, fenofibrate, fentanyl, fexofenadine, finasteride, fluconazole, flurbiprofen, fluvastatin, fosphenyloin, frovatriptan, furazolidone, gabapentin, gemfibrozil, glibenclamide, glipizide, glyburide, glimepiride, griseofulvin, halofantrine, ibuprofen, irbesartan, irinotecan, isosorbide dinitrate, isotretinoin, itraconazole, ivermectin, ketoconazole, ketorolac, lamotrigine, lansoprazole, leflunomide, lisinopril, loperamide, loratadine, lovastatin, L-thryroxine, lutein, lycopene, medroxyprogesterone, mifepristone, mefloquine, megestrol acetate, methadone, methoxsalen, metronidazole, miconazole, midazolam, miglitol, minoxidil, mitoxantrone, montelukast, nabumetone, nalbuphine, naratriptan, nelfinavir, nifedipine, nilsolidipine, nilutamide, nitrofurantoin, nizatidine, omeprazole, oprevelkin, oestradiol, oxaprozin, paclitaxel, paracalcitol, paroxetine, pentazocine, pioglitazone, pizofetin, pravastatin, prednisolone, probucol, progesterone, pseudoephedrine, pyridostigmine, rabeprazole, raloxifene, rofecoxib, repaglinide, rifabutine, rifapentine, rimexolone, ritanovir, rizatriptan, rosiglitazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terazosin, tetrahydrocannabinol, tiagabine, ticlopidine, tirofibran, tizanidine, topiramate, topotecan, toremifene, tramadol, tretinoin, troglitazone, trovafloxacin, ubidecarenone, valsartan, venlafaxine, verteporfin, vigabatrin, vitamin A, vitamin D, vitamin E, vitamin K, zafirlukast, zileuton, zolmitriptan, zolpidem, and zopiclone. Of course, salts, isomers and derivatives of the above-listed hydrophobic active ingredients may also be used, as well combinations and mixtures thereof.

In other embodiments, the active ingredient is hydrophilic, however, combination of hydrophilic, hydrophobic and non-polar agents may also be used. The water solubility for hydrophilic active ingredients is generally greater than about 0.1% by weight, and typically greater than about 1% by weight. Suitable hydrophilic active ingredients include: analgesics, anti-inflammatory agents, antihelminthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, .beta.-Blockers, cardiac inotropic agents, corticosteroids, diuretics, anti-parkinsonian agents, gastro-intestinal agents, histamine receptor antagonists, keratolytics, lipid regulating agents, anti-anginal agents, cox-2 inhibitors, leukotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, and mixtures thereof.

Other hydrophilic active ingredients include: a cytokine, a peptidomimetic, a peptide, a protein, a toxoid, a serum, an antibody, a vaccine, a nucleoside, a nucleotide, a portion of genetic material, a nucleic acid, or a mixture thereof. Other examples of suitable hydrophilic active ingredients include: acarbose; acyclovir; acetyl cysteine; acetylcholine chloride; alatrofloxacin; alendronate; aglucerase; amantadine hydrochloride; ambenomium; amifostine; amiloride hydrochloride; aminocaproic acid; amphotericin B; antihemophilic factor (human), antihemophilic factor (porcine); antihemophilic factor (recombinant), aprotinin; asparaginase; atenolol; atracurium besylate; atropine; azithromycin; aztreonam; BCG vaccine; bacitracin; becalermin; belladona; bepridil hydrochloride; bleomncyin sulfate; calcitonin human; calcitonin salmon; carboplatin; capecitabine; capreomycin sulfate; cefamandole nafate; cefazolin sodium; cefepime hydrochloride; cefixime; cefonicid sodium; cefoperazone; cefotetan disodium; cefotaxime; cefoxitin sodium; ceftizoxime; ceftriaxone; cefuroxime axetil; cephalexin; cephapirin sodium; cholera vaccine; chorionic gonadotropin; cidofovir; cisplatin; cladribine; clidinium bromide; clindamycin and clindamycin derivatives; ciprofloxacin; clodronate; colistimethate sodium; colistin sulfate; corticotropin; cosyntropin; cromolyn sodium; cytarabine; dalteparin sodium; danaparoid; desferrioxamine; denileukin diflitox; desmopressin; diatrizoate meglumine and diatrizoate sodium; dicyclomine; didanosine; dirithromycin; dopamine hydrochloride; dornase alpha; doxacurium chloride; doxorubicin; etidronate disodium; enalaprilat; enkephalin; enoxaparin; enoxaprin sodium; ephedrine; epinephrine; epoetin alpha; erythromycin; esmolol hydrochloride; factor IX; famciclovir; fludarabine; fluoxetine; foscarnet sodium; ganciclovir; granulocyte colony stimulating factor, granulocyte-macrophage stimulating factor; growth hormones—recombinant human; growth hormone—bovine; gentamycin; glucagon; glycopyrolate; gonadotropin releasing hormone and synthetic analogs thereof; GnRH; gonadorelin; grepafloxacin; *haemophilus* B conjugate vaccine; Hepatitis A virus vaccine inactivated; Hepatitis B virus vaccine inactivated; heparin sodium; indinavir sulfate; influenza virus vaccine; interleukin-2; interleukin-3; insulin-human, insulin lispro; insulin procine; insulin NPH; insulin aspart; insulin glargine; insulin detemir; interferon alpha; interferon beta; ipratropium bromide; ifosfamide; Japanese encephalitis virus vaccine; lamivudine; leucovorin calcium; leuprolide acetate, levofloxacin; lincomycin and lincomycin derivatives; lobucavir; lomefloxacin; loracarbef; mannitol; is measles virus vaccine; meningococcal vaccine; menotropins; mepenzolate bromide; mesalamine; methenamine; methotrexate; methscopolamine; metformin hydrochloride; metoprolol; mezocillin sodium; mivacurium chloride; mumps viral vaccine; nedocromil sodium; neostigmine bromide; neostigmine methyl sulfate; neurontin; norfloxacin; octreotide acetate; ofloxacin; olpadronate; oxytocin; pamidronate disodium; pancuronium bromide; paroxetine; perfloxacin; pentamidine isethionate; pentostatin; pentoxifylline; periciclovir; pentagastrin; pentholamine mesylate; phenylalanine; physostigmine salicylate; plague vaccine; piperacillin sodium; platelet derived growth factor-human; pneumococcal vaccine polyvalent; poliovirus vaccine inactivated; poliovirus vaccine live (OPV); polymyxin B sulfate; pralidoxime chloride; pramlintide, pregabalin; propafenone; propenthaline bromide; pyridostigmine bromide; rabies vaccine; residronate; ribavarin; rimantadine hydrochloride; rotavirus vaccine; salmeterol xinafoate; sinealide; small pox vaccine; solatol; somatostatin; sparfloxacin; spectinomycin; stavudine; streptokinase; streptozocin; suxamethonium chloride; tacrine hydrochloride; terbutaline sulfate; thiopeta; ticarcillin; tiludronate; timolol; tissue type plasminogen activator; TNFR:Fc; TNK-tPA; trandolapril; trimetrexate gluconate; trospectinomycin; trovafloxacin; tubocurarine chloride; tumor necrosis factor; typhoid vaccine live; urea; urokinase; vancomycin; valacyclovir; valsartan; varicella virus vaccine live; vasopressin and vasopressin derivatives; vecuronium bromide; vinblastine; vincristine; vinorelbine; vitamin B12; warfarin sodium; yellow fever vaccine; zalcitabine; zanamivir; zolendronate; zidovudine; pharmaceutically acceptable salts, isomers and derivatives thereof; and mixtures thereof.

A wide variety of therapeutically active agents can be used in conjunction with the present invention. The therapeutically active agents (e.g. pharmaceutical agents) which may be used in the compositions of the present invention include both water soluble and water insoluble drugs. Examples of such therapeutically active agents include antihistamines (e.g., dimenhydrinate, diphenhydramine, chlorpheniramine and dexchlorpheniramine maleate), analgesics (e.g., aspirin, codeine, morphine, dihydromorphone, oxycodone, etc.), non-steroidal anti-inflammatory agents (e.g., naproxyn, diclofenac, indomethacin, ibuprofen, sulindac), anti-emetics (e.g., metoclopramide), anti-epileptics (e.g., phenyloin, meprobamate and nitrezepam), vasodilators (e.g., nifedipine, papaverine, diltiazem and nicardirine), anti-tussive agents and expectorants (e.g., codeine phosphate), anti-asthmatics (e.g. theophylline), antacids, anti-spasmodics (e.g., atropine, scopolamine), antidiabetics (e.g., insulin), diuretics (e.g., ethacrynic acid, bendrofluazide), anti-thypotensives (e.g., propranolol, clonidine), antihypertensives (e.g, clonidine, methyldopa), bronchodilators (e.g., albuterol), steroids (e.g., hydrocortisone, triamcinolone, prednisone), antibiotics (e.g., tetracycline), antihemorrhoidals, hypnotics, psycho-tropics, antidiarrheals, mucolytics, sedatives, decongestants, laxatives, vitamins, stimulants (including appetite suppressants such as phenylpropanolamine), as well as salts, hydrates, and solvates of the same. The above list is not meant to be exclusive.

In certain embodiments, the therapeutically active agent comprises hydromorphone, oxycodone, dihydrocodeine, codeine, dihydromorphine, morphine, buprenorphine, salts, hydrates and solvates of any of the foregoing, mixtures of any of the foregoing, and the like. In other embodiments, the active agent is a locally active therapeutic agent and the environment of use may be, e.g., the gastrointestinal tract, or body cavities such as the oral cavity, periodontal pockets, surgical wounds, the rectum or vagina. The liquid formulations of the present invention may be provided orally, topically, subcutaneously, intramuscularly, intraperitoneally, intraocularly, intraossealy, nasally, urethrally, mucosally, vaginally, rectally, intradurally, epidurally and the like. The liquid formulation of the present invention may also be provided as a mist, e.g., to the deep lung (alveolarly).

Locally active pharmaceutical agents of use with the present inveention include antifungal agents (e.g., amphotericin B, clotrimazole, nystatin, ketoconazole, miconazol, etc.), antibiotic agents (penicillins, cephalosporins, erythromycin, tetracycline, aminoglycosides, etc.), antiviral agents (e.g, acyclovir, idoxuridine, etc.), breath fresheners (e.g. chlorophyll), antitussive agents (e.g., dextromethorphan hydrochloride), anti-cariogenic compounds (e.g. metallic salts of fluoride, sodium monofluorophosphate, stannous fluoride, amine fluorides), analgesic agents (e.g., methylsalicylate, salicylic acid, etc.), local anesthetics (e.g., benzocaine), oral anti-septics (e.g., chlorhexidine and salts thereof, hexylresorcinol, dequalinium chloride, cetylpyridinium chloride), anti-flammatory agents (e.g., dexamethasone, betamethasone, prednisone, prednisolone, triamcinolone, hydrocortisone, etc.), hormonal agents (oestriol), antiplaque agents (e.g, chlorhexidine and salts thereof, octenidine, and mixtures of thymol, menthol, methysalicylate, eucalyptol), acidity reducing agents (e.g., buffering agents such as potassium phosphate dibasic, calcium carbonate, sodium bicarbonate, sodium and potassium hydroxide, etc.), and tooth desensitizers (e.g., potassium nitrate). This list is not meant to be exclusive. Other embodiments of the present invention include disinfecting agents, e.g., chlorine compounds such as calcium hypochlorite, and the environment of use is a surrounding body of water, e.g. a recreational pool. The active may be one or more cleansing agents, a germicide, a deodorant, a surfactant, a fragrance, a perfume, a sanitizer, and/or a dye, and the environment of use is an aqueous solution, e.g. a urinal or toilet bowl. Examples of fragrances include: perfume oils, volatile—compounds including esters, ethers aldehydes, alcohols, unsaturated hydrocarbons, terpenes, and other ingredients well known in the art.

The liquid formulation may also include active agents with one or more chemical agents, e.g., fertilizers, animal repellents, insect repellents, pesticides, herbicides, fungicides, plant growth stimulants, and the environment of use is, e.g., anywhere around the home, e.g. soil, trees etc. The fertilizer may be, for example, a nitrogen containing compound such as urea, urea formaldehyde composites, potassium nitrate, potassium sulfate, potassium chloride, ammonium nitrate, ammonium sulfate, monoammonium phosphate, dibasic ammonium phosphate, ammoniated super-phosphoric acid, micronutrient ingredients such as trace elements of iron, zinc, manganese, copper, boron, molybdenum, and mixtures of any of the foregoing. In these embodiments, the thickness of the controlled release coating will depend upon, among other things, the desired rate and overall time period for release of an effective amount of the active agent. In some circumstances where a relatively long time period of efficacy is desired, the substrate may be coated to a relatively high weight gain of, e.g., up to 50% or more.

The examples herein include pharmaceutically active compounds useful in the practice of the present invention, e.g., antihistamines, decongestants, antitussives and/or expectorants. Other actives for use with the present invention include, but are not limited to: non-steroidal anti-inflammatory drugs (NSAIDs) and other analgesic drugs such as acetaminophen and phenacetin. These materials are incorporated into the immediate or controlled release formulations of the invention in amounts governed by the desired release characteristics of the material in such excipient base and such that conventional dosages comply with applicable federal Food and Drug Administration (FDA) or other regulations.

Decongestants useful with the present invention (along with a salt form) are phenylephrine (bitartrate, tannate, HBr, HCl), phenylpropanolamine (HCl) and pseudoephedrine (HCl). Furthermore, a number of herbal and/or natural decongestants are known in the art, all of which may be used with the present invention.

Expectorants for use with the present invention include, e.g., guaifenesin, terpin hydrate, (glyceryl guaiacolate), potassium (iodide, citrate) and potassium guaicolsulfonate. Other expectorants, whether individual ingredients or combinations of ingredients may be used with the present invention. Furthermore, a number of herbal and/or natural expectorants are known in the art, all of which may be used with the present invention, e.g., Oregano Leaf Extract 25-500 mg (which may be a liquid extract), Red Clover 25-500 mg, Buckthorn Root 25-500 mg, or Fenugreek 25-500 mg, or mixtures thereof.

Examples of antihistamines for use with the present invention (e.g., in salt form) are chlorpheniramine (maleate), brompheniramine (maleate), dexchlorpheniramine (maleate), dexbrompheniramine (maleate), triprolidine (HCl), diphenhydramine (HCl), doxylamine (succinate), tripelennamine (HCl), cyproheptatine (HCl), bromodiphenhydramine (HCl), phenindamine (tartrate), pyrilamine (maleate, tannate) and azatadine (maleate). Antitussives that may be used with the present invention (with salt form) include: caramiphen (edisylate), dextromethorphan (HBr) and codeine (phosphate, sulfate). A number of herbal and/or natural antihistamines are known in the art, all of which may be used with the present invention.

Other actives may also be included with the present invention, e.g., non-steroidal anti-inflammatory drugs (NSAIDs) such as propionic acid derivatives; acetic acid derivatives; fenamic acid derivatives; biphenylcarboxylic acid derivatives; and oxicams. Examples of propionic acid derivatives include: ibuprofen, naproxen, ketoprofen, flurbiprofen, fenoprofen, suprofen, fenbufen, and fluprofen may be mentioned as preferred compounds. Acetic acid derivatives derivatives include: tolmetin sodium, zomepirac, sulindac and indomethacin. Fenamic acid derivatives derivatives include: mefenamic acid and meclofenamate sodium. Diflunisal and flufenisal are biphenylcarboxylic acid derivatives, while oxicams include piroxicam, sudoxicam and isoxicam. Other analgesics for use with the present invention include acetominophen and phenacetin. Naproxen may be present in amounts of about 50 to about 250 milligrams per liquid dose, however, naproxen may be used in amounts of between about 100 and about 150 milligrams per liquid dose.

Phenylephrine may be present in amounts of between about 15 and about 60 milligrams per liquid dose. Phenylephrine is generally in amounts of about 5 to about 30 milligrams per liquid dose, with half or less of that amount used in a pediatric form of the formulation. In one example of the present invention, phenylephrine is provided in the amount of about 15 mg for extended release. Phenylephrine hydrochloride is an orally effective nasal decongestant. Chemically it is (S)-3-hydroxy-α[(methylamino) methyl]benzenemethanol hydrochloride. Phenylepherine is a synthetic, optically active sympathomimetic amine that has one hydroxyl group on the benzene ring. The hydroxyl group is placed in the position meta to the aliphatic side chain. The meta position affords optimal activity and phenylepherine (neo-synephrine) replaced an older preparation, synephrine, in which the hydroxyl was in the para position.

Phenylephrine hydrochloride is available in the form of the levorotatory isomer, a white, odorless, non-hygroscopic, crystalline compound possessing a bitter taste. Phenylephrine hydrochloride has a melting point of 140-145 degrees C. and is freely soluble in water and alcohol. Decongestant compounds in the form of their free bases as well as their salts, e.g., hydrochloride, citrate, maleate, tannate, etc., are well known.

Dextromethorphan may be present in amounts of between about 5 and about 20 milligrams per liquid dose, with a general range of about 10 to about 15 milligrams. Brompheniramine may be present in amounts of between about 0.5 and about 4.0 milligrams per liquid dose with a general range of about 2.0 milligrams per liquid dose. Half or less of that amount may be used in a pediatric form of the formulation.

The present invention may also include chlorpheniramine, which is an antihistamine used to relieve, e.g., allergic rhinitis (seasonal allergy). The symptoms of allergic rhinitis include: sneezing, runny nose, itching, and watery eyes. Chlorpheniramine may also be used to treat immediate allergic reactions. Chlorpheniramine may be provided alone and in combination with other prescription or nonprescription drugs, e.g., to treat symptoms of allergy, colds, and upper respiratory infections.

The present invention may also include one or more analgesics, e.g., acetaminophen may be present in amounts of up to about 600 milligrams per liquid dose. Generally, acetaminophen is present in amounts of about 50 to about 200 milligrams per liquid dose. Another example is ibuprofen, which may be used in amounts of, e.g., 150 milligrams, with a range of about 50 and about 150 milligrams per dose being used generally. Half or less of that amount may be used in a pediatric form of the formulation.

In one example of the present invention, an expectorant (e.g., Guaifenesin DC) is provided at lower doses and is made available immediately for absorption, followed by a lower dose of a decongestant (e.g., phenylephrine) which is release slowly over, e.g., about 1 to 8 hrs. This release profile makes the product more efficacious since the large amount of expectorant begins to break up mucus prior to the time the decongestant is released to provide long acting decongestant activity after mucus breakdown has begun.

Generally, guaifenesin is present in amounts of about 10 to about 600 milligrams per liquid dose. Guaifenesin may be present in amounts of 100, 150, 200, 300, 400, 440, 500 or even 600 or more milligrams per liquid dose. In one example, guaifenesin is present in amounts of about 100 to about 200 milligrams per liquid dose, with half or less of that amount used in a pediatric form of the formulation.

In one example, 400 milligrams of guaifenesin are included as an active for immediate release. Guaifenesin is an expectorant that increases the output of phlegm (sputum) and bronchial secretions by reducing adhesiveness and surface tension. The increased flow of less viscous secretions promotes cilliary action and facilitates the removal of mucus.

Hence, expectorants such as guaifenesin change a dry, unproductive cough to one that is more productive and less frequent. Guaifenesin, known chemically as 3(2-methoxyphenoxy)-1,2-propanediol, is a crystalline powder soluble in water and alcohol. It is indicated in the USP Drug information as an expectorant for the symptomatic relief of cough due to colds and minor upper respiratory infections.

Excipients for use with the present invention are well known to those of skill in the art and include humectants such as glycerin and propylene glycol, preservatives such as sodium benzoate and paraben, sweeteners such as sodium saccharin, corn syrup and sorbitol solutions, menthol and various flavoring and coloring agents. The pharmaceutically active compounds and excipients for human use should be of N.F. or U.S.P. grade.

For certain actives it may be useful to provide buffering agents (or bufferants), where the acid is a pharmaceutically acceptable acid, such as hydrochloric acid, hydrobromic acid, hydriodic acid, sulfuric acid, nitric acid, boric acid, phosphoric acid, acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid, and where the base is a pharmaceutically acceptable base, such as an amino acid, an amino acid ester, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanolamine, ethylenediamine, triethanolamine, triethylamine, triisopropanolamine, or a salt of a pharmaceutically acceptable cation and acetic acid, acrylic acid, adipic acid, alginic acid, alkanesulfonic acid, an amino acid, ascorbic acid, benzoic acid, boric acid, butyric acid, carbonic acid, citric acid, a fatty acid, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, and uric acid.

In some formulations additives may also include: chelating agents (such as EDTA and EDTA salts); colorants or opaquants (such as titanium dioxide, food dyes, lakes, natural vegetable colorants, iron oxides, silicates, sulfates, magnesium hydroxide and aluminum hydroxide); coolants (e.g., trichloroethane, trichloroethylene, dichloromethane, fluorotrichloromethane); cryoprotectants (such as trehelose, phosphates, citric acid, tartaric acid, gelatin, dextran and mannitol); and diluents or fillers (such as lactose, mannitol, talc, magnesium stearate, sodium chloride, potassium chloride, citric acid, spray-dried lactose, hydrolyzed starches, directly compressible starch, microcrystalline cellulose, cellulosics, sorbitol, sucrose, sucrose-based materials, calcium sulfate, dibasic calcium phosphate and dextrose).

Substrates. A powder constitutes a finely divided (milled, micronized, nanosized, precipitated) form of an active ingredient or additive molecular aggregates or a compound aggregate of multiple components or a physical mixture of aggregates of an active ingredient and/or additives. Such substrates may be formed of various materials known in the art, such as, for example: sugars, such as lactose, sucrose or dextrose; polysaccharides, such as maltodextrin or dextrates; starches; cellulosics, such as microcrystalline cellulose or microcrystalline cellulose/sodium carboxymethyl cellulose; inorganics, such as dicalcium phosphate, hydroxyapitite, tricalcium phosphate, talc, or titania; and polyols, such as mannitol, xylitol, sorbitol or cyclodextrin.

It should be emphasized that a substrate need not be a solid material, although often it will be a solid. For example, the encapsulation coat on the substrate may act as a solid "shell" surrounding and encapsulating a liquid, semi-liquid, powder or other substrate material. Such substrates are also within the scope of the present invention, as it is ultimately the carrier, of which the substrate is a part, which must be a solid.

Excipients. The solid pharmaceutical compositions suspended in the liquid formulation of the present invention may include optionally one or more additives, sometimes referred to as additives. The excipients may be contained in an encapsulation coat in compositions, which include an encapsulation coat, or can be part of the solid carrier, such as coated to an encapsulation coat, or contained within the components forming the solid carrier. Alternatively, the excipients can be contained in the pharmaceutical composition but not part of the solid carrier itself.

Solubilizers. The pharmaceutical compositions of the present invention may include optionally one or more solubilizers, i.e., additives to increase the solubility of the pharmaceutical active ingredient or other composition components in the solid carrier. It has been recognized by the present inventors that guaifenesin, in fact, acts as a solubilizer for phenylephrine, and is used as such in the examples provided herein. Other solubilizers are known in the art. Mixtures of solubilizers are also within the scope of the invention and are readily available from standard commercial sources.

The amount of solubilizer that may be included in compositions of the present invention is not particularly limited. Of course, when such compositions are administered to a patient, the amount of a given solubilizer is limited to a bioacceptable amount, which is readily determined by one of skill in the art. In some circumstances, it may be advantageous to include amounts of solubilizers far in excess of bioacceptable amounts, for example, to maximize the concentration of active ingredient, with excess solubilizer removed prior to providing the composition to a patient using conventional techniques, such as distillation or evaporation.

The following are general instructions common to most liquid manufacturing as will be known to the skilled artisan. For example, first, it is determined is all of the raw materials are available for this manufacturing process. All of the raw materials are checked for correct identity and Quality Assurance release. All personnel involved in the manufacturing process must be familiar with the active ingredients Material Safety Data Sheet and for those involved in the manufacturing process, these must wear appropriate attire and use the appropriate safety equipment. Standard microbiological precautions are followed, e.g., avoidance of contact with the raw materials and use of gloves during the manufacturing process. When using water, water purity is verified and use of a Purified Water System is recommended. Prior to use allow the water to run to waste for 15 seconds. Assure that the water quality is greater than 14 megohm-cm (MΩ-cm) on the second deionized water finishing tank.

FIG. 1 is a flow chart 100 that summarizes the basic steps in the method of the present invention. In this flow chart 100, four basic branches and processing steps or systems are used to reach a final mixing or blending step (102), each of which provides one component that may be used with the present invention. In block 104, a thickening agent is added to a vessel or container that will provide, e.g., density control to the final solution. The thickening agent, e.g., a syrup (corn, rice, wheat, soy, maple, pine) is heated to decrease its viscosity (block 106) for a sufficient time to provide an even temperature and/or decrease its viscosity without burning the thickener. In block 108, water (room temperature or heated) is slowly added to the thickening agent along the sides of the vessel and at a rate that minimizes the introduction of air or bubbles to the thickening agent. The mixing step will generally use below the surface mixing, as with a propeller driven, variable speed mixer at speeds and rates that minimize, reduce or eliminate blade cavitation, thereby reducing the amount of gas or air that enters the mixture. The blended water and thickener are then allowed to rest at block 110 and are stored pending further steps.

In block 112, one or more preservatives are added to a vessel or container and dissolved in accordance with the manufacturers instructions, e.g., by adding a solvent (block 114) that may be water or a polar or non-polar solvent. Again, the mixing and blending will be conducted so as to minimize the introduction of air or bubbles into the mixture. To further reduce the likelihood of bubble formation, in block 116, a surfactant is added, again taking care to minimize bubble formation. In some cases it may be appropriate to de-gas the solution at this stage by, e.g., applying a vacuum or allowing the mixture to settle. Finally, in block 118, the preservative/surfactant mixture is blended and stored for further processing. The mixing step will generally use below the surface mixing, as with a propeller driven, variable speed mixer at speeds and rates that minimize, reduce or eliminate blade cavitation, thereby reducing the amount of gas or air that enters the mixture.

In another branch of the flow chart 100, a thixotropic agent is added (block 120) to a vessel and the water is added. The water added to the thixotropic agent may be room temperature or higher to allow the thixotropic agent to swell (block 122). Finally, once the thixotropic agent has swelled it is mixed to clarify to the maximum extent possible at block 124. Again, the mixing step will generally use below the surface mixing, as with a propeller driven, variable speed mixer at speeds and rates that minimize, reduce or eliminate blade cavitation, thereby reducing the amount of gas or air that enters the mixture.

The one or more active agents are selected and prepared (block 126), obtained or purchased. The amount of active is calculated and the appropriate amounts are weighted (block 128). If the active is not pre-coated, in block 130, the beads, particles, polymers, resins, etc. may be coated as described hereinbelow or using any number of coating materials and methods known to the skilled artisan. Generally, the density and/or coefficient of viscosity of the final coated particles with the active agent will be at, around or about that of the combined thickening and thixotropic agent (to minimize the need for mixing of the liquid formulation prior to use). One advantage of using a thixotropic agent is that it reduces the need to closely match the densities of the active particles and the final solution, as the thixotropic agent "gels" when standing, thereby limiting the amount of settling of the active during a normal, short-term dosing period (e.g., 1-day to 2 weeks). Finally, the active agents (which may still be dry) may be mixed with one or more excipients, coating, flavorings, color and the like (which may also be dry) and the mixture is blended (block 132).

The four branches depicted in flow chart 100 may be combined into less or divided into more branches depending on the actives, excipients, thickeners and thixotropic agents used. For example, is the actives are dry and the colorants, flavorants, etc., are not, then these may be added to a liquid solution (e.g., at blocks 110, 118 and/or 124). It may also be advantageous to mix actives (beads, particles, polymers, etc.) in with liquid portions and/or in water.

Example 1

Capsule shells and process: 7.5% phenylephrine immediate release beads where used as starting material. A portion of this lot was transferred to a rotating pan. Phenylephrine was added to the beads using of pharmaceutical glaze. The beads were then allowed to roll and cure for 6 hours before sustained release coating was added. In-order to develop the product, four different levels of sustained release coating amounts were added. In one example, 10.93 Kgs of phenylephrine were added to the beads using 4.32 Kgs of pharmaceutical glaze. The beads were then allowed to roll and cure for 6 hours before sustained release coating was added. Alternatively, the encapsulation coat may be prepared by air suspension chilling, air suspension drying, compression, cryopelletization, encapsulation, extrusion, lyophilization, molding, spheronization, spray chilling, spray congealing, and spray drying.

In order to develop the product four different levels of sustained release coating amounts were added. The first was 7.15 kg's of SR mix #1 and 4.96 kg's of pharmaceutical glaze. Once this loading was complete 5.0 kg's were removed for drying and testing. The second load consisted of 4.75 kg's of SR mix #1 and 2.68 kg's of pharmaceutical glaze. Again 5.0 kg's of beaded material was removed for drying at 40° C. and testing. The third load consisted of 5.92 kg's SR mix #1 and 3.43 kg's of glaze. After application another 5.0 kg's of beaded material was removed from the pan for drying at 40° C. and testing. The fourth and final load consisted of 7.78 kg's of SR mix #1 and 4.56 kg's of pharmaceutical glaze. The entire pan was allowed to roll and cure under heat lamps for 6 hours before sampling for study.

Below is a list of all theoretical percentages and actual assay results for the, above, described material.

| SR Mix | Theoretical PEH % | Actual PEH % | Dissolution | | |
|---|---|---|---|---|---|
| | | | 90 min, | 3 hr, | 6 hr |
| #1 | 21.6% | 20.8% | 4.6%, | 18.6%, | 59.3% |
| #2 | 19.8% | 19.3% | 0.2%, | 0.8%, | 11.0% |
| #3 | 17.8% | 17.3% | 0.16%, | 0.4%, | 2.7% |
| #4 | 15.5% | 15.4% | 0.6%, | 0.8%, | 2.6% |

Based on assay and dissolution profile load #1 was selected for use in further development. The moisture content in load #4 may be higher than those loads dried in the tray drier. This may have contributed to why load #3 and #4 have essentially the same dissolution profile despite the increased SR mix.

Dissolution: It was found that the dissolution rate of the phenylephrine is accelerated when combined with Gauifenesin DC. Due to this effect the testing of the dissolution rate is achieved by first making a mock-up of the finished product. By doing so the suitability of the phenylephrine beads was determined more accurately. Direct specifications for dissolution were determined once data was collected to accurately predict this rate change.

Example 2

Ionic Resin Mix

Another method of controlling the rate of availability involves using controlled release matrices. One such controlled release bead includes adding one or more active agents to one or more resins or polymers. To control the rate of dissolution one or more of the following may be used: Dextromethorphan Polistirex Resin (15% ETC); Pseudoephedrine Polistirex Resin (15% ETC); and/or Chlorpheniramine Polacrilex Resin (15% ETC). These resins may be used to deliver therapeutically effective amounts of Chlorpheniramine Polacrilex equivalent to Chlorpheniramine Maleate 6 mg/Dextromethorphan Polistirex equivalent to Dextromethorphan HBr 30 mg/Pseudoephedrine Polistirex equivalent to Pseudoephedrine HCl 30 mg per 5 ml dose.
Table 1—Basic Liquid Suspension

| Item Description | Amount per 5 ml Dose | Quantity required |
| --- | --- | --- |
| Purified Water, USP | — | 874 kg |
| High Fructose Corn Syrup | 2800.00 mg | 1120 kg |
| Propylene Glycol, USP Split into 3 parts - 50 kg/ 95 kg/10 kg | 387.50 mg | 155 kg |
| Methylparaben | 1.00 mg | 0.40 kg |
| Propylparaben | 0.25 mg | 0.10 kg |
| Polysorbate 80 | 25.00 mg | 10.0 kg |
| Xanthan Gum, NF (Rhodigel 200) | 14.00 mg | 5.60 kg |
| Red Opatint Dye (DG-15008) | 1.50 mg | 0.60 kg |
| Strawberry Flavor (133.19035) | 5.25 mg | 2.10 kg |

If only one lot of raw material Dextromethorphan Polistirex Resin (15% ETC) is required, the Assay Value is calculated and entered in the quantity required in kg (Dextromethorphan Polistirex Resin) column and in the Total quantity required in kg (Dextromethorphan Polistirex Resin) area.

If multiple lots of Dextromethorphan Polistirex Resin are required, multiply the calculated Assay Value of the partial lot(s) of Dextromethorphan Polistirex Resin by the kg available [quantity required in kg (Dextromethorphan Polistirex Resin)] to get the value. These values are recorded in the conversion factor column and enter the kg available of the partial(s) in the [quantity required in kg (Dextromethorphan Polistirex Resin)] column.

Divide the remaining conversion factor required by the calculated Assay Value of the lot of Dextromethorphan Polistirex Resin used to complete the weigh-up and enter the result in the corresponding quantity required in kg (Dextromethorphan Polistirex Resin) column. Total the quantity required in kg (Dextromethorphan Polistirex Resin) and enter this value in the Total quantity required in kg (Dextromethorphan Polistirex Resin) area.

Divide each quantity required in kg (Dextromethorphan Polistirex Resin) by 0.4 (this 0.4 is a conversion factor for, e.g., a 2000 Liter batch size) and enter the result(s) in the Amount per Dose in mg (Dextromethorphan Polistirex Resin) column. Total these values and enter the result in the Total Amount per Dose in mg (Dextromethorphan Polistirex Resin) area. The quantity required in kg is transferred (Dextromethorphan Polistirex Resin) and the amount per dose in mg (Dextromethorphan Polistirex Resin) results to the Formula & Weighup Sheet.

If only one lot of raw material (Pseudoephedrine Polistirex Resin) is required, divide the conversion factor of 34.63 by the calculated Assay Value and enter the result in the quantity required in kg (Pseudoephedrine Polistirex Resin) column and in the Total quantity required in kg (Pseudoephedrine Polistirex Resin) area. Enter the conversion factor column or N/A are required.

If multiple lots of Pseudoephedrine Polistirex Resin are required, multiply the calculated Assay Value of the partial lot(s) of Pseudoephedrine Polistirex Resin by the kg available [quantity required in kg (Pseudoephedrine Polistirex Resin)] to get the Partial conversion factor. Enter the value in the conversion factor column. Enter the kg available of the partial(s) in the [quantity required in kg (Pseudoephedrine Polistirex Resin)] column. Subtract the Partial conversion factor(s) from 34.63 to determine the remaining conversion factor required. Enter this value in the appropriate space.

Divide the remaining conversion factor required by the calculated Assay Value of the lot of Pseudoephedrine Polistirex Resin used to complete the weigh-up and enter the result in the corresponding quantity required in kg (Pseudoephedrine Polistirex Resin) column. Total the quantity required in kg is determined and (Pseudoephedrine Polistirex Resin) this value is entered in the total quantity required in kg (Pseudoephedrine Polistirex Resin) area. Divide each quantity required in kg (Pseudoephedrine Polistirex Resin) by 0.4 (this 0.4 is a conversion factor for, e.g., a 2000 Liter batch size) and enter the result(s) in the Amount per Dose in mg (Pseudoephedrine Polistirex Resin) column. Total these values and enter the result in the Total Amount per Dose in mg (Pseudoephedrine Polistirex Resin) area. The quantity required in kg is transferred (Pseudoephedrine Polistirex Resin) and the amount per dose in mg (Pseudoephedrine Polistirex Resin) results to the Formula & Weighup Sheet.

If only one lot of raw material (Pseudoephedrine Polistirex Resin) is required, divide the conversion factor of 8.08 by the calculated Assay Value and enter the result in the quantity required in kg (Chlorpheniramine Polacrilex Resin) column and in the Total quantity required in kg (Chlorpheniramine Polacrilex Resin) area. Enter 8.08 in the conversion factor column and N/A the unrequired rows.

If multiple lots of Chlorpheniramine Polacrilex Resin are required, multiply the calculated Assay Value of the partial lot(s) of Chlorpheniramine Polacrilex Resin by the kg available [quantity required in kg (Chlorpheniramine Polacrilex Resin)] to get the Partial conversion factor. Enter this (these) value(s) in the conversion factor column. Enter the kg available of the partial(s) in the [quantity required in kg (Chlorpheniramine Polacrilex Resin)] column.

Subtract the Partial conversion factor(s) from 8.08 to determine the remaining conversion factor required. Divide the remaining conversion factor required by the calculated Assay Value of the lot of Chlorpheniramine Polacrilex Resin used to complete the weigh-up and enter the result in the corresponding quantity required in kg (Chlorpheniramine Polacrilex Resin) column.

Total the quantity required in kg (Chlorpheniramine Polacrilex Resin) and enter this value in the Total quantity required in kg (Chlorpheniramine Polacrilex Resin) area. Divide each quantity required in kg (Chlorpheniramine Polacrilex Resin) by 0.4 (this 0.4 is a conversion factor for a 2000 Liter batch size) and enter the result(s) in the Amount per Dose in mg (Chlorpheniramine Polacrilex Resin) column. Total these values and enter the result in the Total Amount per Dose in mg (Chlorpheniramine Polacrilex Resin) area. Transfer the quantity required in kg (Chlorpheniramine Polacrilex Resin) and the Amount per Dose in mg (Chlorpheniramine Polacrilex Resin) results to the Formula & Weighup Sheet.

Resin Blending Instructions. Again, all personnel involved in the manufacturing process must wear appropriate attire and use the appropriate safety equipment. Rooms and blnder, e.g., a 20 ft3 V-Blender, are first checked for cleanliness and the observations are record in the Cleaning, Maintenance & Use Log(s). All equipment, utensils, and containers are also checked for cleanliness and the room, equipment, and containers labeled as required.

Transfer Methocel to the Blender. Blend for 2 minutes. Next, add Dextromethorphan Polistirex Resin to the Blender, Pseudoephedrine Polistirex Resin and Chlorpheniramine Polacrilex Resin to the Blender. Blend for 5 minutes. Discharge the Blender into 2 separate medium sized, pre-weighted, plastic-lined containers (≈36 kg each) labeled "Resin Blend". Make sure that all of the material is removed from the blender and put aside for preparation of the liquid formulation.

TABLE 2

Basic 3 Active Blend

| Item Description | Amount per 5 ml Dose |
|---|---|
| Dextromethorphan Polistirex Resin (15% ETC) | 30 mg |
| Pseudoephedrine Polistirex Resin (15% ETC) | 30 mg |
| Chlorpheniramine Polacrilex Resin (15% ETC) | 6 mg |
| Methocel E5LV (hydroxypropyl methylcellulose, USP) | 19.25 mg |
| Purified Water, USP | qs |

TABLE 3

Basic Two Active Blend

| Item Description | Amount per 5 ml Dose |
|---|---|
| Pseudoephedrine Polistirex Resin (15% ETC) | 30 mg |
| Chlorpheniramine Polacrilex Resin (15% ETC) | 6 mg |
| Methocel E5LV (hydroxypropyl methylcellulose, USP) | 19.25 mg |
| Purified Water, USP | qs |

Suspension Blending Instructions. All personnel involved in the manufacturing process must wear appropriate attire and use the appropriate safety equipment. When using the Diaphragm Pump(s) allow the solution supply valve to be opened and the liquid from the feed solution is allowed to prime the pump prior to starting the pump. This is done to prevent the introduction of air into the feed solution. When using the Diaphragm Pump(s) to transfer any solution containing Propylene Glycol make sure that the lines are completely drained to avoid the introduction of water into the solution.

Check room and the oven (or heating device) and check the Processing Sweep Tank for cleanliness. All steps in the process should generally by recorded in the Cleaning, Maintenance & Use Log(s). Check room and appropriately sized Open Top Processing Tank for cleanliness. Set up a Diaphragm Pump(s) and check for cleanliness. Record in the Cleaning, Maintenance & Use Log(s). Set up an 87 gallon Plastic Processing Tank, e.g., an 87 gallon processing tank, with a mixer and check for cleanliness. Set up an appropriately sized Electric Kettle and check for cleanliness. Verify the cleanliness of the disassembled valves, hoses & connections, and other miscellaneous equipment/hardware. Check all utensils and containers for cleanliness. Label the room, equipment, and containers as required.

Figure 2:
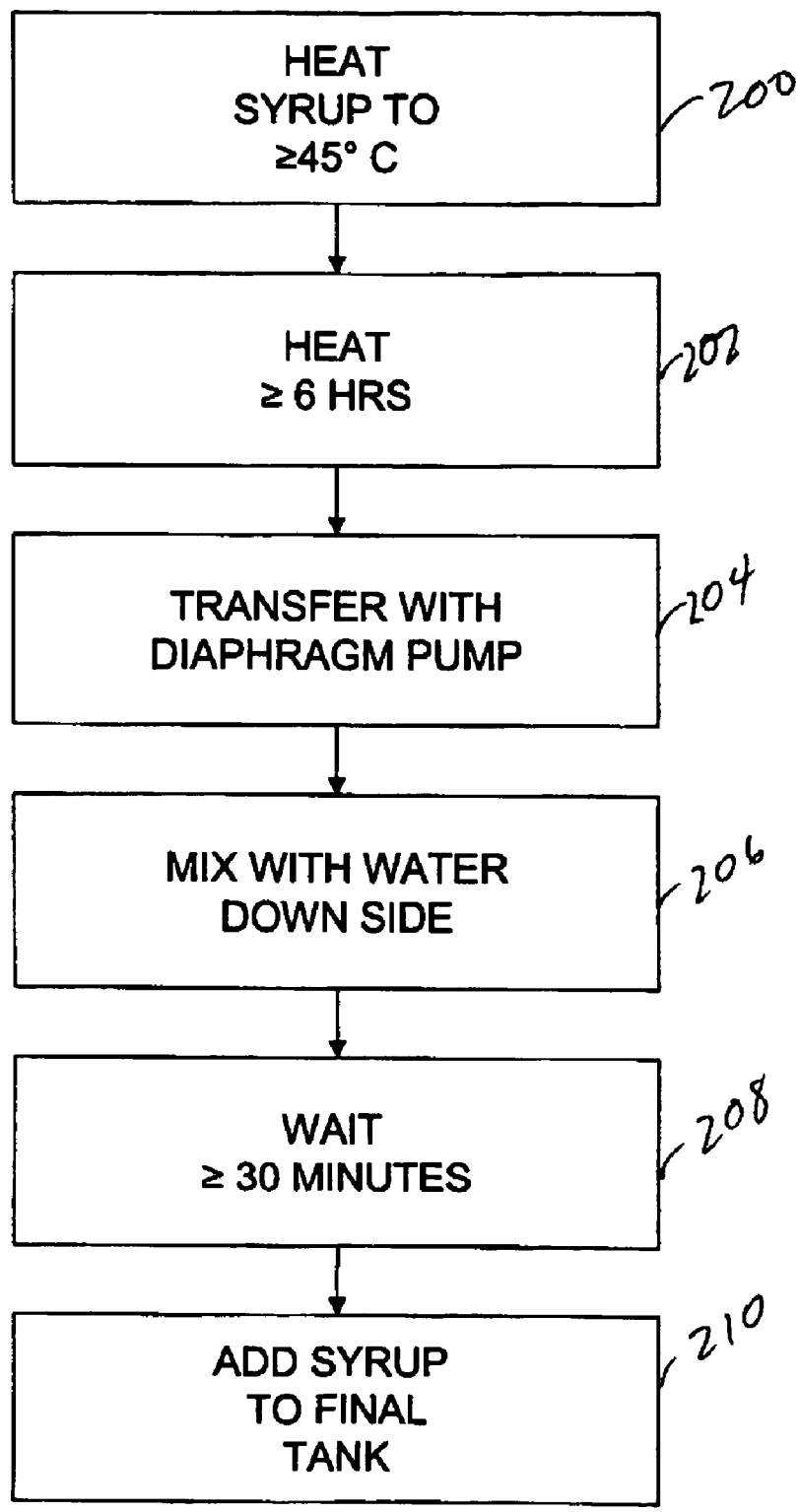
FIG. 2 is a detailed flow chart of present invention.

As shown in FIG. 2, the thickening branch of the method is depicted. First, the valves and connections of all the vessels or containers are checked to ensure that they are clean and that all valves are in the closed position. In block 200, the syrup is heated, e.g., corn syrup is placed in the heater/oven or alternate heating device at ≈45° C. for 8 to 12 hours (generally greater than 6 hours, block 202). Next, in block 204, the thickening agent is transferred, e.g., corn syrup to the Processing Sweep Tank using a diaphragm pump or like pump that minimizes or generally eliminates the introduction of air or air bubbles into the syrup. If adding the thickening agent from the top of a vessel, the flow of the syrup from the pump to the tank should be directed to the side of the tank at a volume and with flow slow enough that the syrup slides down the side of the tank introduces as little air as possible into the syrup, e.g., in a large batch 800 liters (block 206) and the thickener and water are mixed with a low or reduced cavitation propeller mixer, paddle mixer and the like. Alternatively, the vessel itself may be heated thereby eliminating the need for transfer of the liquid; however, in such circumstances the thickening agent should still be introduced into the vessel so as to minimize bubble formation. In block 208, the thickener or syrup is allow to rest for about 30 minutes or more to allow the syrup to settle and if necessary to allow for cooling and or reduction of the temperature to, e.g., room temperature. In block 210, the thickener is prepared for transfer into a larger vessel for final mixing using, e.g., a diaphragm or other like pump.

For transfer of the thickener or syrup, the lines for transfer will be flushed and/or primed through the diaphragm pump with, e.g., 20 kg of purified water to the processing sweep tank. For final transfer to a larger final tank, the flow from the pump to the tank should be directed to the side of the tank slow enough that the corn syrup/purified water slides down the side of the tank, introducing as little air as possible. Allow the corn syrup to sit undisturbed (usually about 30 minutes) to allow any air bubbles to subside.

Figure 3:
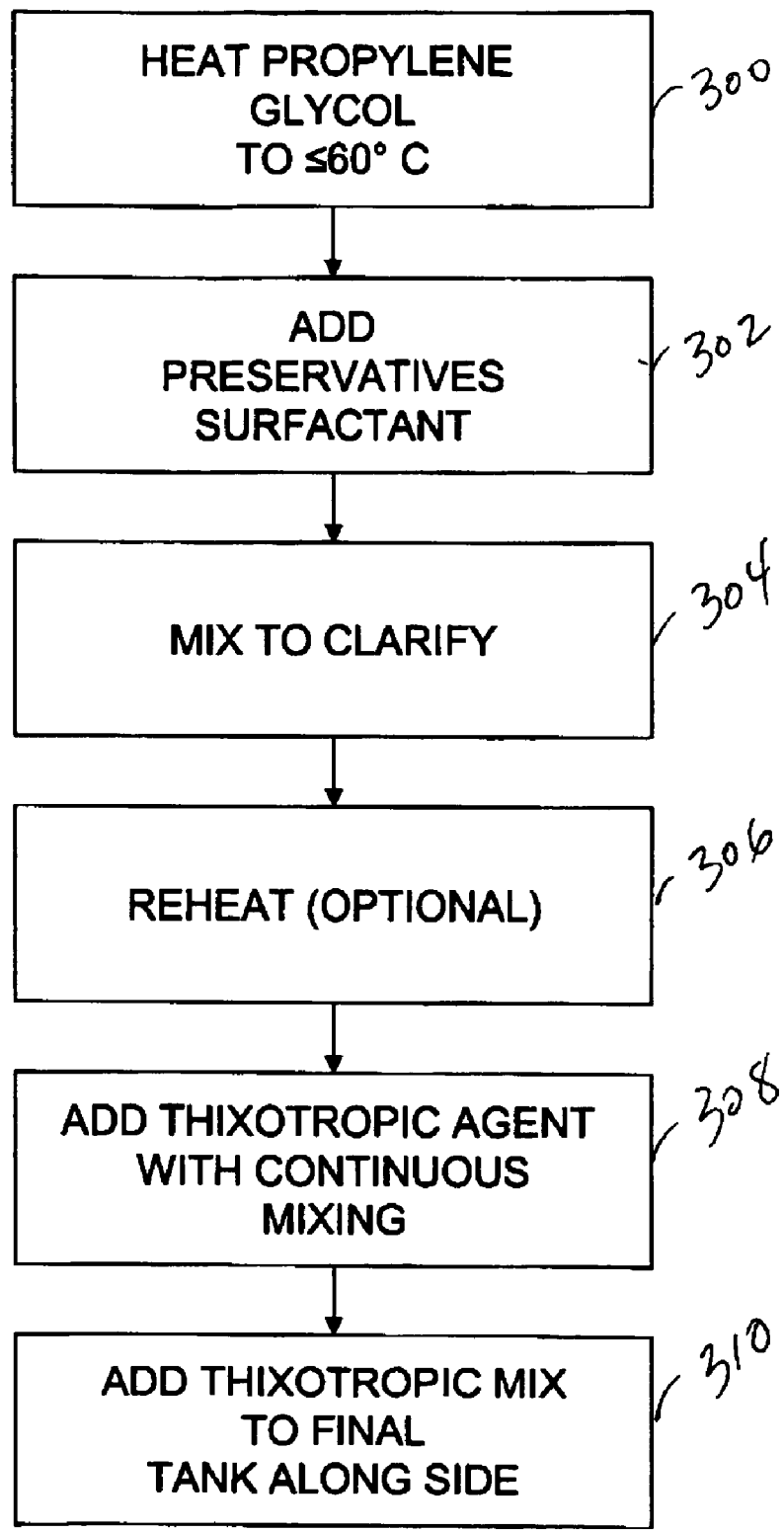
FIG. 3 is another detailed flow chart of present invention.

FIG. 3 summarizes the preparation of a polyethylene glycol preservative mix. Transfer approximately 800 kg of purified water to the open top processing tank using the diaphragm pump (if needed) transfer the 50 kg portion of propylene glycol to the electric kettle and heat this propylene glycol up to but not to exceed 60° C.) (block 300). Next, in block 302 a preservative, e.g., methylparaben and/or propylparaben to the electric kettle. Label the kettle "paraben solution". The parabens may be transferred to the kettle at any point during the heating process. Intermittently mix the paraben solution in the electric kettle until dissolved. Also in block 302, a surfactant and/or emulsifying agent, e.g., polysorbate 80, is added to the kettle containing the "paraben solution" and mix until the two phases combine to form one clear phase. If the temperature of the solution has cooled significantly it may need to reheated (not to exceed 60° C.) to form one clear phase. Label the kettle "paraben/polysorbate 80 solution." Transfer the 95 kg portion of propylene glycol to a plastic processing tank. Transfer the "paraben/polysorbate 80 solution" to the 87 gallon plastic processing tank. Rinse the electric kettle to the 87 gallon plastic processing tank with the 10 kg portion of propylene glycol. In block 304 the mixture is mixed to clarify the mixture and optionally heated in block 306. In block 308, thixotropic agent is added with continuous mixing and in block 310 the thixotropic mixture is added to the final tank.

Figure 4:
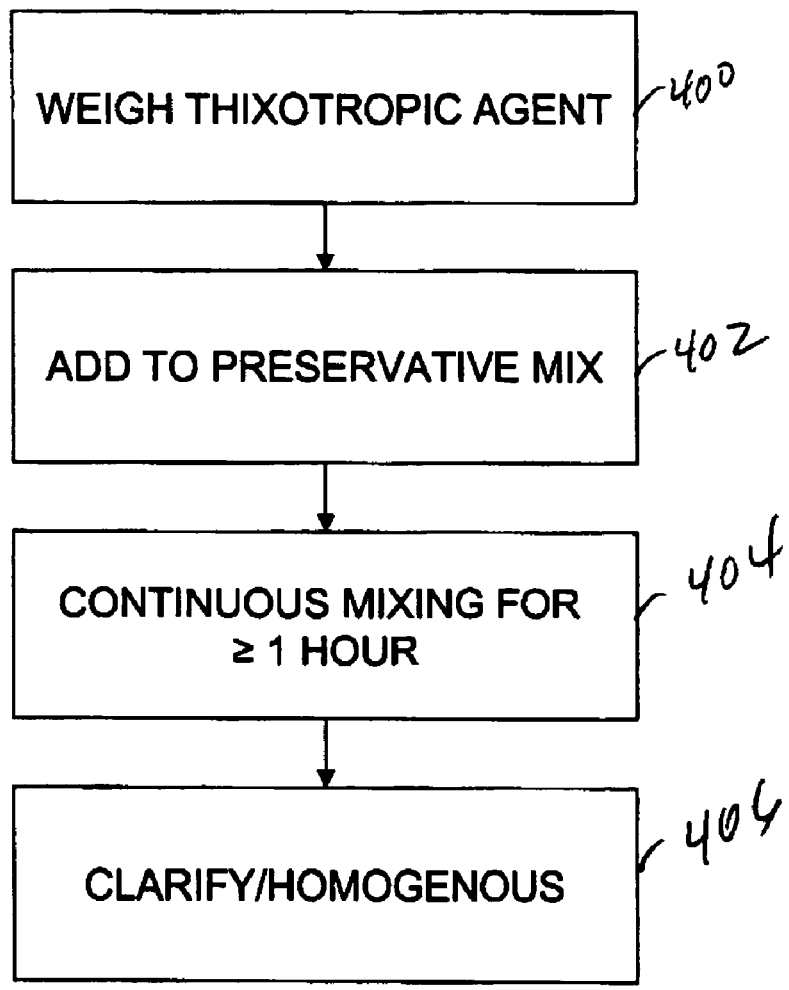
FIG. 4 is another detailed flow chart of present invention.

FIG. 4 is flow chart of the method for preparing a thixotropic agent. In block 400, a thixotropic agent such as xanthan gum, is added to, e.g., the "paraben/polysorbate 80 solution" in a processing tank and mix to slurry (usually about 10 minutes)(block 402). The xanthan gum will generally not dissolve in this slurry, therefore, it is preferable that the slurry not be allowed to stand without mixing because the xanthan gum will settle (block 404). Finally, in block 406, processing tank's mixer is turned on and the mixture is clarified and/or made generally homogenous, taking care to minimize bubble formation for about 1 hour or more. The mixer may remain "on" for the remainder of the manufacturing process.

Figure 5:
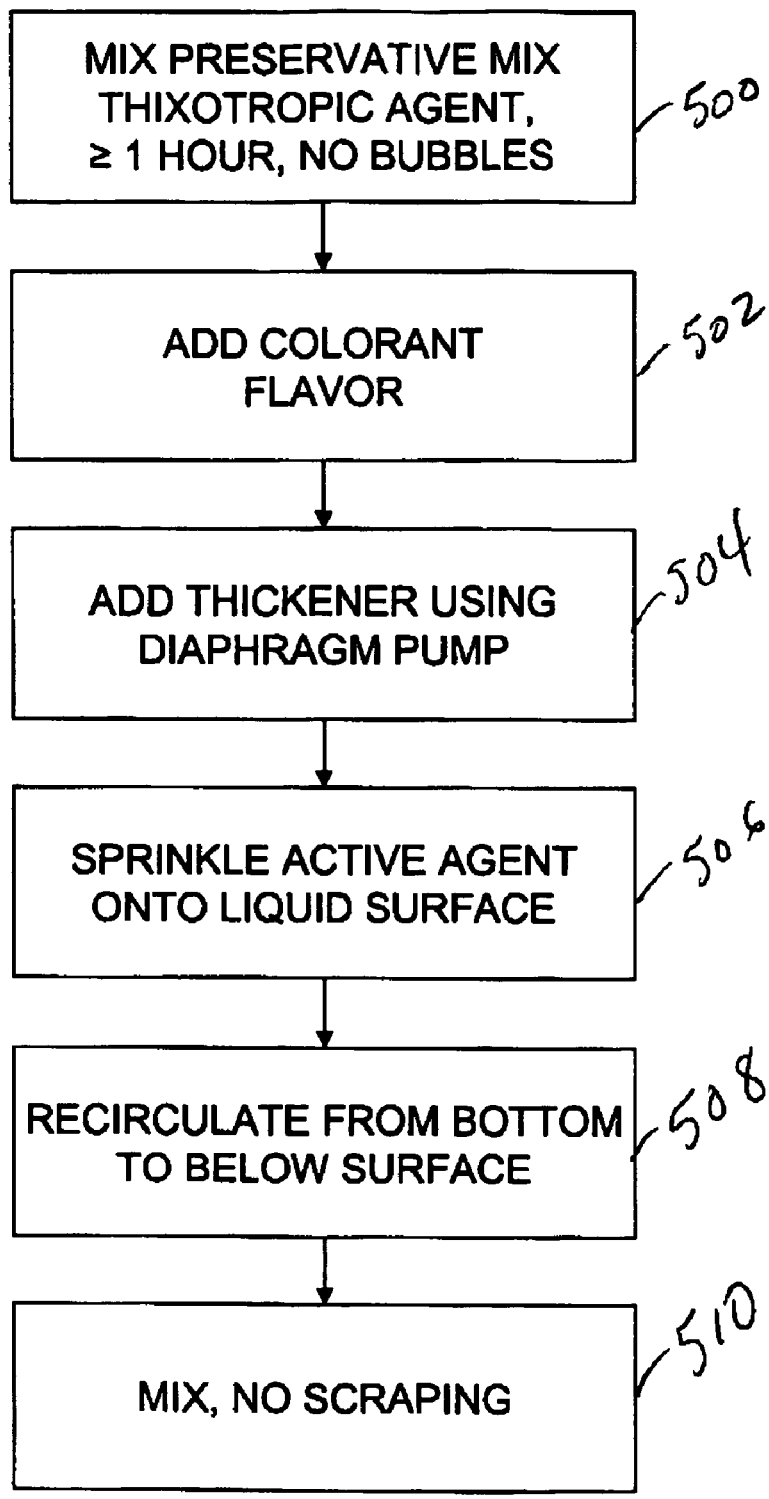
FIG. 5 is a flowchart with the final steps of the present invention.

As shown in FIG. 5, the preservative mix, e.g., the paraben/polysorbate 80/xanthan gum mixture, is transferred to the open top processing tank (block 500). Again, the flow of the solution to the tank should be directed to the side of the tank so that as little air as possible is introduced. Mix the solution in the open top processing tank for a minimum of 1 hour, without introducing any air, until the solution is homogeneous (uniform appearance with no visible lumps). Next, in block 502, a colorant is added, e.g., red opatint dye, and flavorant, e.g., strawberry flavor to the open top processing tank. Rinse each container to the open top processing tank with approximately 2 kg of purified water. At block 506, gradually sprinkle the "resin blend" to the open top processing tank. Continue mixing for a minimum of 30 minutes, without introducing any air, until the solution is homogeneous (uniform appearance with no visible lumps). Alternatively, using the diaphragm pump carefully transfer the solution in the open top processing tank to the processing sweep tank containing the thickening agent (block 504), e.g., the corn syrup. The flow of the solution from the open top processing tank to the processing sweep tank should be directed below the surface of the corn syrup introducing as little air as possible (block 508). Rinse the open top processing tank to the processing sweep tank with approximately 50 kg of purified water. Install the electric mixer in the processing sweep tank and submerge the propeller to the interface of the corn syrup and the solution from the open top processing tank. Angle the mixer propeller so that it does not interfere with the tank sweepers and it does not introduce air to the solution during operation or scrape the sides of the vessel or tank.

Turn the sweepers of the processing sweep tank on at the minimum speed to check for clearance in relation to the propeller of the electric interface mixer (block 510), without adding the scrapers or spatulas that are often used with general liquid mixing. Increase the speed of the tank sweepers to, e.g., 45 Hertz and turn on the tank mixer to, e.g., 31 Hertz. While still running the tank sweepers and the tank mixer, turn on the electric interface mixer and mix for 15 minutes. If any air is being introduced into the solution turn off the electric interface mixer immediately and repeat the prop angle adjustment/sweeper interference procedure.

Using the diaphragm pump at a maximum of, e.g., 30 psi recirculate the solution in the processing sweep tank for 15 minutes. The flow of the solution from the pump to the tank should be directed approximately one foot below the surface of the suspension introducing as little air as possible. Turn off and remove the electric interface mixer and increase the speed of the tank sweepers to, e.g., 90 Hertz while maintaining the tank mixer at 31 Hertz. Unless otherwise specified, the tank sweepers and mixer should remain on throughout the remainder of the manufacturing and packaging process.

Turn off the sweepers (leave the mixer on) to the processing sweep tank and remove the recirculation pipe prior to this qs step. Using the diaphragm pump qs to, e.g., 2400 kg with purified water. The flow of purified water from the pump to the tank should be directed to the side of the tank slow enough that it slides down the side of the tank introducing as little air as possible. Immediately after the qs step has been completed, turn the tank sweepers back on at, e.g., 90 Hertz.

Reinstall the recirculation pipe approximately one foot below the surface of the suspension. Continue to sweep and mix, along with recirculation using the diaphragm pump at a maximum of, e.g., 30 psi, the solution in the processing sweep tank for, e.g., 45 minutes. Generally and depending on the materials, the following steps should be performed quickly so that the solution does not sit without mixing. Assure that all mixing is off (recirculation should remain on) and remove a small sample in a clear container.

Notify quality assurance that the batch is ready for sampling if the tests performed in prior steps are acceptable. Sample the batch below the surface using the sampling tool. Make sure that the appropriate samples are removed. Turn the sweeper (at 45 Hertz) and mixer (at 31 Hertz) back on. Reset the recirculation pipe (at 30 psi) so that it is 1 foot from the agitation plate of the sweeper. Unless otherwise specified herein, these settings may remain constant. Make sure that a 10 mesh in-line filter is installed after the pump used to transfer the suspension to the packaging line.

Figure 6:
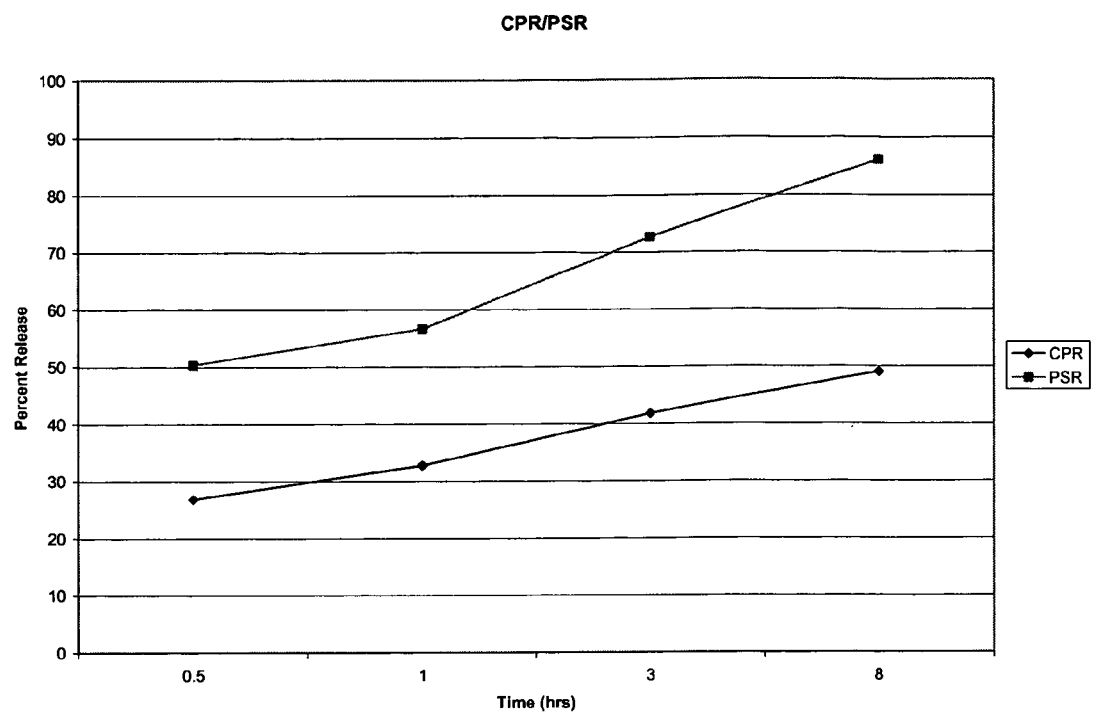
FIG. 6-8 are graphs that demonstrate the release profile of two active agents in a liquid formulation of the present invention.
Figure 7:
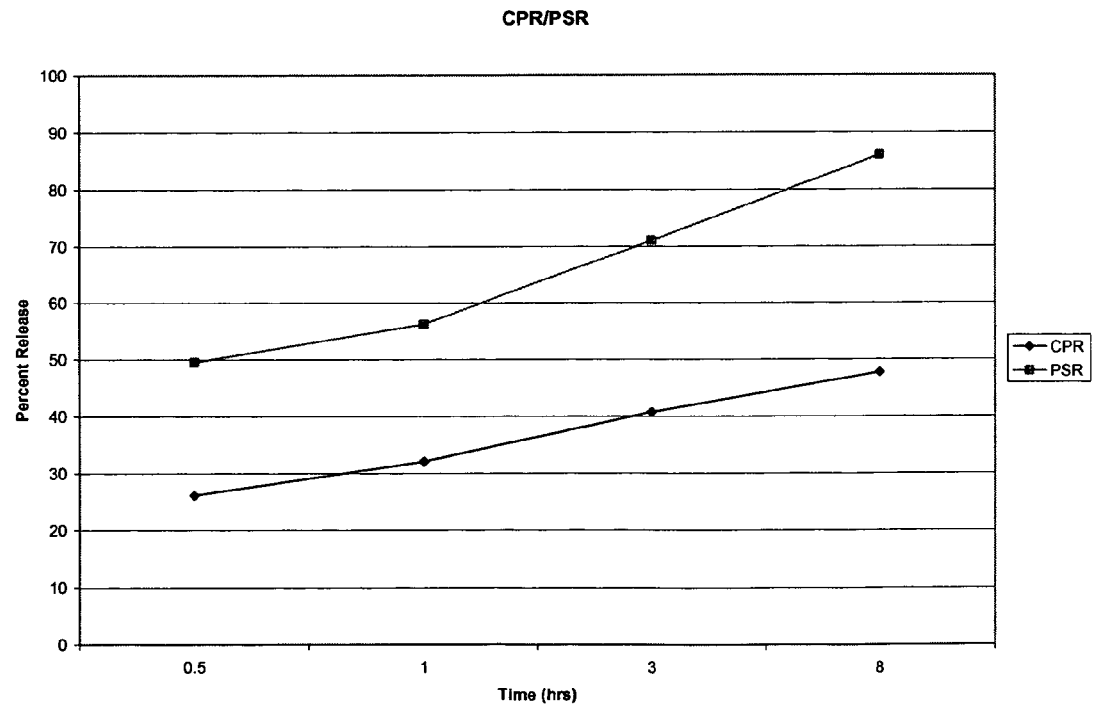
Figure 8:
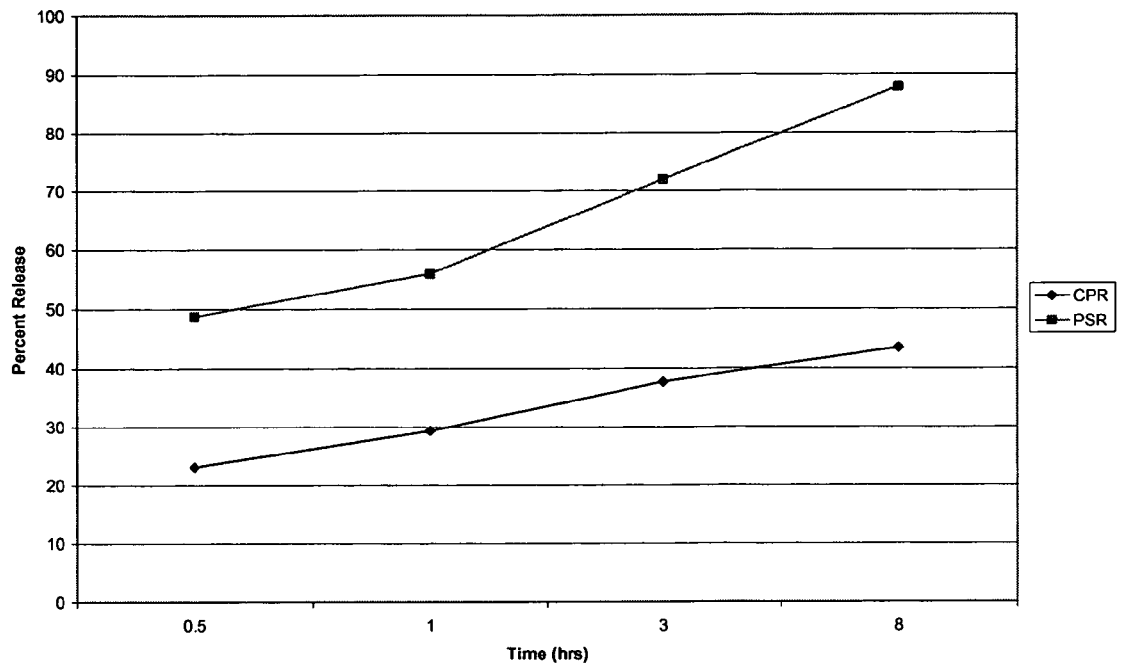

FIG. 6-8 are graphs that demonstrate the release profile of two active agents in a liquid formulation of the present invention. The dissolution profiles of active agents in a sustained-release liquid formulation of the present invention was tested using, e.g., a standard low pH or a water dissolution profile assays. Briefly, the sustained release actives were tested for percent release by dissolution in a 37 degree Celsius water bath in one liter of deionized water into which 5.0 grams of potassium chloride was dissolved with paddles that mix the sample at 150 revolutions per minute (RPMs). A 5 milliliter test sample of the liquid formulation, neat or titrated, is added to the bath using a syringe (which may be washed in the water/KCl mix). Aliquots of 2 ml are sampled at, e.g., 0.5, 1, 3 and 8 hours. The results of a two active agent formulation and release are shown for three different samples in FIGS. 6-8. The exact formulation used was taught hereinabove in example 2.

Figure 9:
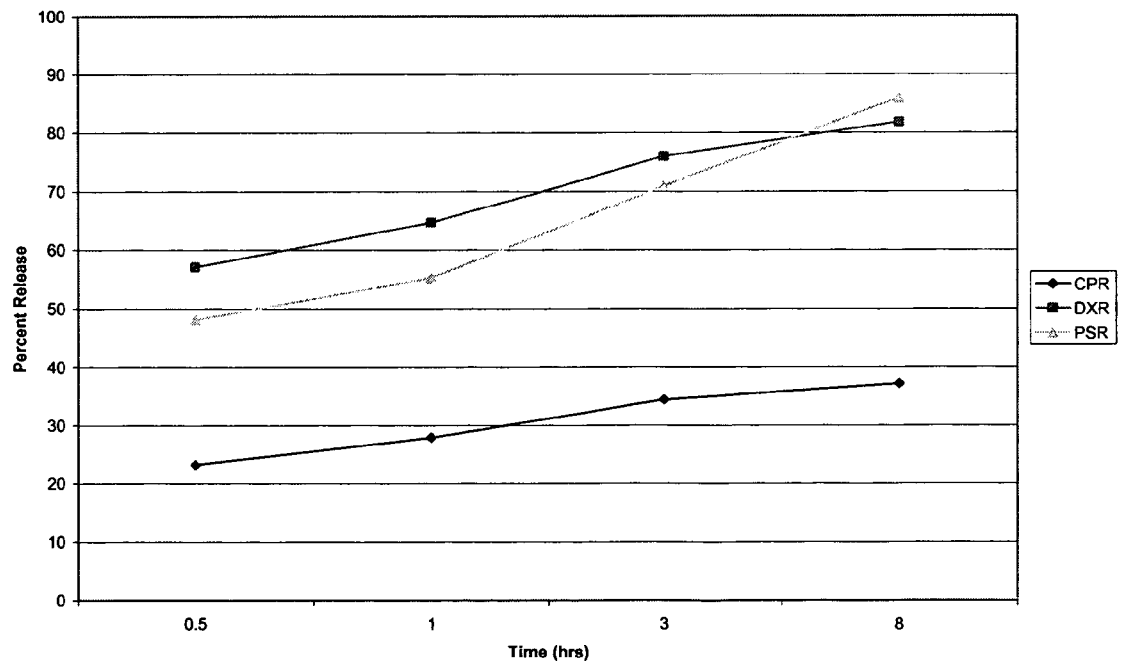
FIG. 9-11 are graphs that demonstrate the release profile of third active agents in a liquid formulation of the present invention.
Figure 10:
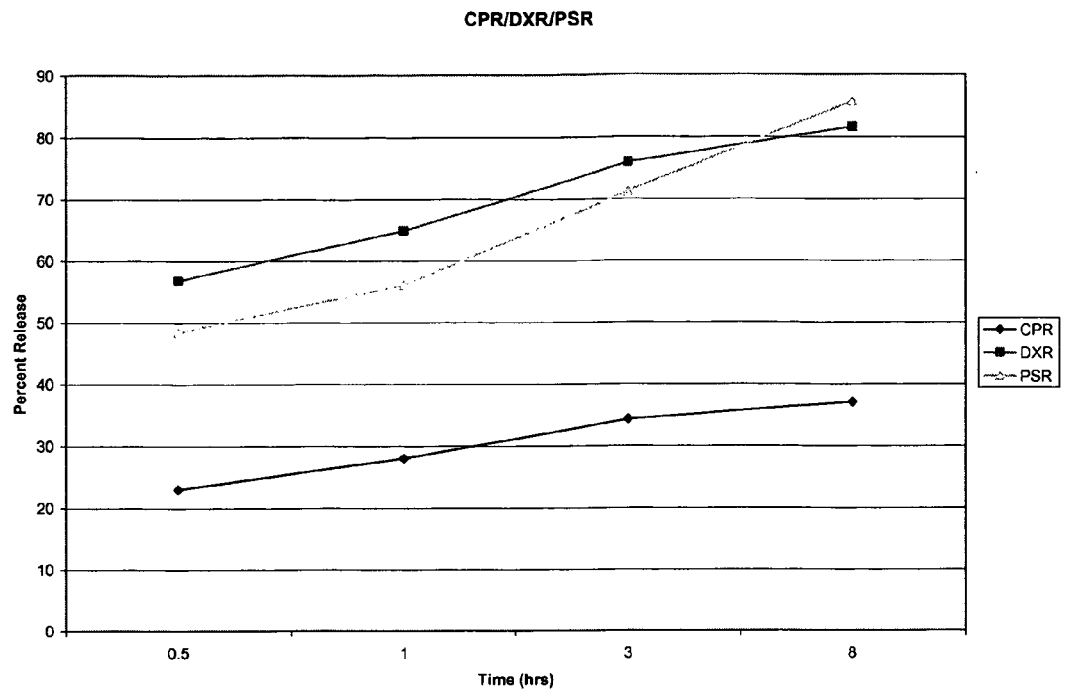
Figure 11:
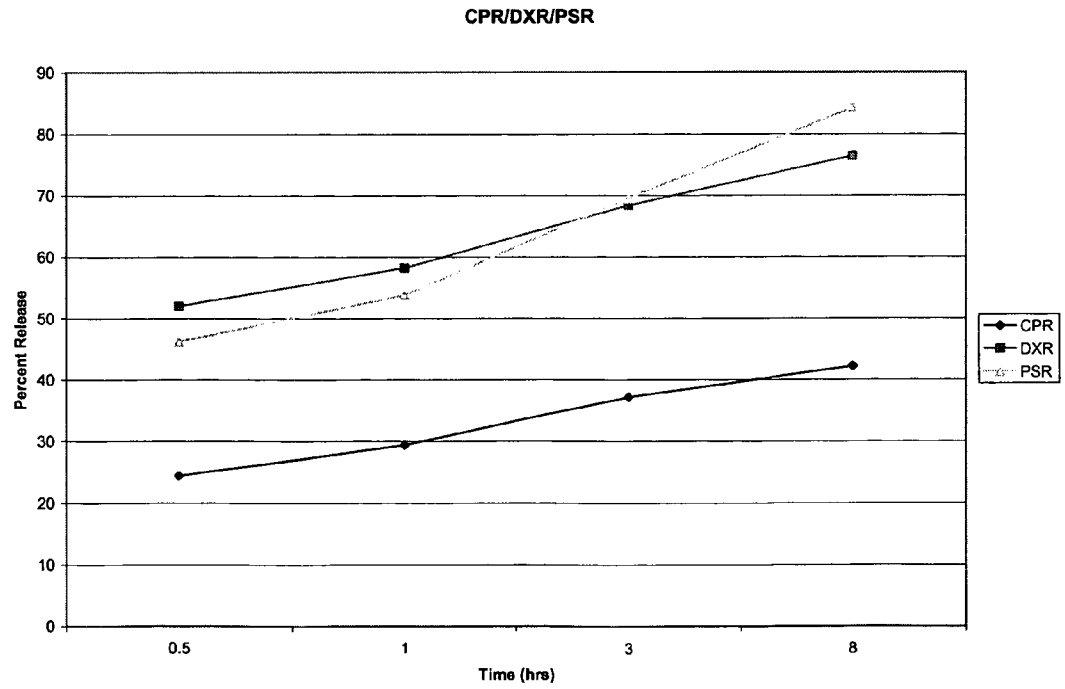

FIG. 9-11 are graphs that demonstrate the release profile of third active agents in a liquid formulation of the present invention. These graphs demonstrate the release profile of three active agents in a liquid formulation of the present invention. The dissolution profiles of active agents in a sustained-release liquid formulation of the present invention was tested using, e.g., a standard low pH or a water dissolution profile assays. Briefly, the sustained release actives were tested for percent release by dissolution in a 37 degree Celsius water bath in one liter of deionized water into which 5.0 grams of potassium chloride was dissolved with paddles that mix the sample at 150 revolutions per minute (RPMs). A 5 milliliter test sample of the liquid formulation, neat or titrated, is added to the bath using a syringe (which may be washed in the water/KCl mix). Aliquots of 2 ml are sampled at, e.g., 0.5, 1, 3 and 8 hours. The results of a three active agent formulation and release are shown for three different samples in FIGS. 6-8.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for preparing a liquid, controlled-release formulation comprising the steps of:
obtaining one or more controlled release microbeads comprising one or more active agents in coated drug-resin complexes;
preparing a dense, thixotropic solution having a density that is at or about the density of the one or more microbeads, wherein the dense, thixotropic solution comprises a thixotropic agent, water and one or more preservatives under conditions that reduce bubble formation; and
mixing the microbeads and the thixotropic solutions under conditions that minimize the introduction of bubbles in the liquid, wherein said method prepares a shelf-stable, liquid controlled-release formulation having a uniform appearance with no visible lumps.

2. The method of claim 1, wherein the one or more microbeads comprise one or more of the following: an enteric coat, a resin coat, a lacquer coat, a pH-sensitive coating, a biodegradable polymer matrix, a water soluble matrix, an ionic matrix, combinations and mixtures thereof.

3. The method of claim 1, wherein the one or more microbeads comprise one or more polymers selected from the group consisting of cellulose, ethylcellulose, methylcellulose, propylcellulose, methoxypropylcellulose, cellulose nitrate, poly(vinyl alcohol), poly(vinyl chloride), polystyrene, polyethylene, polypropylene, poly(ethylene-co-vinyl acetate), poly(hydroxybutyric acid), poly(hydroxyvalerianic acid-co-hydroxybutyric acid), poly(lactic acid), poly(glycolic acid), poly(lactic acid-co-glycolic acid), poly(ε-caprolactones), poly(ε-caprolactone-co-DL-lactic acid), poly(maleic anhydride), polyamides, gelatin, chitosan, collagen, poly(hydroxyalkyl)-L-glutamines, poly(γ-ethyl-L-glutaminate-co-glutamic acid), poly(L-leucine-co-L-aspartic acid), poly(proline-co-glutamic acid), poly(alkyl 2-cyanoacrylates), polyurethanes, poly(methyl methacrylate), poly(methyl methacrylate-co-methacrylic acid) and poly(methacrylate-co-hydroxypropyl methacrylate), polystirex, salts, combinations and mixtures thereof.

4. The method of claim 1, wherein reduced bubble formation comprises the step of using a diaphragm pump to combine the water and the thixotropic agent and one or more preservatives, colorants and flavorants.

5. The method of claim 1, wherein reduced bubble formation comprises the step of placing the recirculating tube below the surface of the liquid.

6. The method of claim 1, wherein reduced bubble formation comprises the step of adding liquids along the side of a vessel holding the liquid.

7. The method of claim 1, wherein reduced bubble formation comprises the step of sprinkling the beads onto the surface of the liquid.

8. The method of claim 1, wherein reduced bubble formation comprises the step of mixing the solution in the absence of one or more paddles that scrape the vessel.

9. The method of claim 1, wherein reduced bubble formation comprises the step of using a diaphragm pump to combine one or more of the water, the thixotropic agent, the one or more preservatives, colorants and flavorants.

10. The method of claim 1, wherein reduced bubble formation comprises the steps of:
placing a recirculating tube below the surface of the liquid;
adding liquids along the side of a vessel holding the liquid; and
using a mixer that lacks scraping paddles.

11. The method of claim 1, wherein reduced bubble formation comprises the step of mixing the solution with a propeller mixer.

12. The method of claim 1, wherein reduced bubble formation comprises the step of mixing the solution with a propeller mixer at a speed that reduces cavitation.

13. The method of claim 1, wherein reduced bubble formation comprises the step of mixing the solution with a propeller that minimizes cavitation.

14. The method of claim 1, wherein a portion of the one or more beads comprises an immediate release profile and another portion comprise a delayed release profile.

15. The method of claim 1, wherein the formulation further comprises one or more flavorants, one or more surfactants, one or more dissolved active agents, one or more buffers, one or more excipients, and mixtures and combinations thereof.

16. The method of claim 1, wherein the one or more active agents are pharmaceutical agents.

17. The method of claim 1, wherein the one or more active agents comprise vitamins, minerals, nutritional supplements, herbal extracts, gums, gels, oils, salts, mixtures and combinations thereof.

18. The method of claim 1, wherein the one or more active agents are pharmaceutical agents selected from protein, peptide, carbohydrate, polysaccharide, glycoprotein, lipid, hormone, growth factor, cytokine, interferon, receptor, antigen, allergen, antibody, antiviral, antifungal, antihelminthic, substrate, metabolite, cofactor, inhibitor, drug, pharmaceutical, nutrient, toxin, poison, explosive, pesticide, chemical warfare agent, biowarfare agent, biohazardous agent, infectious agent, prion, radioisotope, vitamin, heterocyclic aromatic compound, carcinogen, mutagen, narcotic, amphetamine, barbiturate, hallucinogen, combinations and mixtures thereof.

19. The method of claim 1, wherein the one or more active agents comprise a pharmaceutical agent, an enzyme, a cytokine, a growth promoting agent, an antibody, an antigen, a hormone, a vaccine, a cell, a live-attenuated pathogen, a heat-killed pathogen, a virus, a bacteria, a fungi, a peptide, a carbohydrate, a nucleic acid, a lipid, mixtures and combinations thereof.

20. The method of claim 1, wherein the one or more active agents is selected from wherein the one or more agents may be steroids, respiratory agents, sympathomimetics, local anesthetics, antimicrobial agents, antiviral agents, antifungal agents, antihelminthic agents, insecticides, antihypertensive agents, antihypertensive diuretics, cardiotonics, coronary vasodilators, vasoconstrictors, β-blockers, antiarrhythmic agents, calcium antagonists, anti-convulsants, agents for dizziness, tranquilizers, antipsychotics, muscle relaxants, drugs for Parkinson's disease, respiratory agents, hormones, non-steroidal hormones, antihormones, vitamins, antitumor agents, miotics, herb medicines, antimuscarinic, interfereons, immunokines, cytokines, muscarinic cholinergic blocking agents, mydriatics, psychic energizers, humoral agents, antispasmodics, antidepressant drugs, anti-diabetics, anorectic drugs, anti-allergenics, decongestants, expectorants, antipyretics, antimigrane, anti-malarials, anti-ulcerative, peptides, anti-estrogen, anti-hormone agents, antiulcer agents, anesthetic agent, drugs having an action on the central nervous system, protein, peptide, carbohydrate, polysaccharide, glycoprotein, lipid, hormone, growth factor, cytokine, interferon, receptor, antigen, allergen, antibody, substrate, metabolite, cofactor, inhibitor, drug, pharmaceutical, nutrient, toxin, poison, explosive, pesticide, chemical warfare agent, biowarfare agent, biohazardous agent, infectious agent, prion, radioisotope, vitamin, heterocyclic aromatic compound, carcinogen, mutagen, narcotic, amphetamine, barbiturate, hallucinogen, and vaccines against virus, bacterium, fungi, helminth, cancer, *Salmonella, Streptococcus, Brucella, Legionella, E. coli, Giardia, Cryptosporidium, Rickettsia*, spore, mold, yeast, algae, amoebae, dinoflagellate, unicellular organism, pathogen, combinations and mixtures thereof.

21. The method of claim 1, wherein the one or more active agents comprises Pseudoephedrine, salts thereof or mixtures of salts thereof.

22. The method of claim 1, wherein the one or more active agents comprises an antihistamine.

23. The method of claim 1, wherein the one or more active agents comprises Chlorpheniramine, salts thereof or mixtures of salts thereof.

24. The method of claim 1, wherein the one or more active agents comprises Dextromethorphan, salts thereof or mixtures of salts thereof.

25. The method of claim 1, wherein the one or more active agents comprises an analgesic.

26. The method of claim 1, wherein the one or more active agents comprises an antitussive.

27. The method of claim 1, wherein the one or more active agents comprises a narcotic.

28. The method of claim 1, wherein the one or more active agents are disposed on a polystirex bead.

29. The method of claim 1, wherein the one or more active agents are disposed on a polypropylene bead.

30. The method of claim 1, wherein the one or more active agents are disposed on a polyethylene bead.

31. The method of claim 1, wherein the one or more active agents are disposed on a polacrilex bead.

32. The method of claim 1, wherein the one or more active agents are disposed on a poly-lactic acid (PLA), poly-glycolic acid (PGA) and/or poly-lactic polyglycolic acid (PGLA) bead.

33. A method for preparing a liquid, controlled-release formulation comprising the step of blending one or more controlled release beads comprising one or more active agents in coated drug-resin complexes with a dense, thixotropic solution with a density that is at or about the density of the one or more beads, wherein the dense, thixotropic solution comprises a thixotropic agent, water and one or more preservatives under conditions that minimize air bubbles which cling to said beads, wherein said method prepares a shelf-stable, liquid controlled-release formulation having a uniform appearance with no visible lumps.

34. The method for preparing a liquid, controlled-release formulation of claim 33, comprising the step of blending a mixture comprising one or more controlled-release beads comprising one or more active agents in coated drug-resin complexes, a thickening agent and a surfactant by mixing with a low cavitation propeller and recirculating the mixture under the surface of the mixture so as to minimize bubble formation.

* * * * *

UNITED STATES PATENT AND TRADEMARK OFFICE
CERTIFICATE OF CORRECTION

| | | |
|---|---|---|
| PATENT NO. | : 8,318,210 B2 | Page 1 of 1 |
| APPLICATION NO. | : 11/068124 | |
| DATED | : November 27, 2012 | |
| INVENTOR(S) | : Tengler et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,443 days.

Signed and Sealed this
Twenty-eighth Day of October, 2014

Michelle K. Lee
*Deputy Director of the United States Patent and Trademark Office*